United States Patent
Millar et al.

(10) Patent No.: US 11,116,155 B2
(45) Date of Patent: Sep. 14, 2021

(54) SYSTEMS AND METHODS FOR BYPASSING HARVESTING FOR A GROW POD

(71) Applicant: Grow Solutions Tech LLC, Lehi, UT (US)

(72) Inventors: Gary Bret Millar, Highland, UT (US); Mark Gerald Stott, Eagle Mountain, UT (US); Michael Stephen Hurst, Farmington, UT (US); Taylor John Woodbury, Provo, UT (US)

(73) Assignee: GROW SOLUTIONS TECH LLC, Vineyard, UT (US)

( * ) Notice: Subject to any disclaimer, the term of this patent is extended or adjusted under 35 U.S.C. 154(b) by 627 days.

(21) Appl. No.: 15/984,663

(22) Filed: May 21, 2018

(65) Prior Publication Data

US 2018/0359973 A1    Dec. 20, 2018

Related U.S. Application Data

(60) Provisional application No. 62/519,665, filed on Jun. 14, 2017, provisional application No. 62/519,661, (Continued)

(51) Int. Cl.
*A01G 9/08* (2006.01)
*A01G 7/04* (2006.01)
(Continued)

(52) U.S. Cl.
CPC ........... *A01G 31/042* (2013.01); *A01D 91/00* (2013.01); *A01G 7/045* (2013.01); *A01G 9/088* (2013.01); *A01G 9/143* (2013.01); *G01N 33/025* (2013.01)

(58) Field of Classification Search
CPC ....... A01D 91/00; A01G 31/042; A01G 9/143
See application file for complete search history.

(56) References Cited

U.S. PATENT DOCUMENTS

| 3,771,258 A | * | 11/1973 | Charney | A01G 9/143 47/65 |
| 5,255,618 A | * | 10/1993 | Berry | A01C 7/042 111/200 |

(Continued)

FOREIGN PATENT DOCUMENTS

| JP | 2002291357 A | 10/2002 |
| JP | 2013000087 A | 1/2013 |

(Continued)

OTHER PUBLICATIONS

International Search Report for PCT/US2018/034063 dated Nov. 26, 2018.

*Primary Examiner* — Peter M Poon
*Assistant Examiner* — Morgan T Barlow
(74) *Attorney, Agent, or Firm* — Dinsmore & Shohl LLP

(57) ABSTRACT

A system bypasses harvesting in an assembly line grow pod when it is determined that a plant in a cart is not ready to harvest. The system includes a track, a cart configured to move on the track, one or more sensors and a controller. The cart includes an upper plate that supports a plant. The controller receives information about the plant from the one or more sensors, determines whether the plant in the cart is ready to harvest based on the information; and transmits an instruction for bypassing harvesting the plant in the cart in response to determination that the plant in the cart is not ready to harvest.

20 Claims, 13 Drawing Sheets

Related U.S. Application Data filed on Jun. 14, 2017, provisional application No. 62/519,304, filed on Jun. 14, 2017.

(51) Int. Cl.
   *A01G 31/04* (2006.01)
   *A01D 91/00* (2006.01)
   *A01G 9/14* (2006.01)
   *G01N 33/02* (2006.01)

(56) References Cited

U.S. PATENT DOCUMENTS

| | | | |
|---|---|---|---|
| 5,438,794 A * | 8/1995 | Wi | A01G 9/143 47/17 |
| 5,956,897 A * | 9/1999 | Takashima | A01G 31/00 47/1.01 R |
| 6,056,064 A * | 5/2000 | deVries | A01G 20/12 172/20 |
| 9,021,739 B2 | 5/2015 | Koo et al. | |
| 9,565,812 B2 | 2/2017 | Wilson | |
| 2006/0185860 A1* | 8/2006 | Brouwer | A01G 20/15 172/19 |
| 2011/0120002 A1* | 5/2011 | Pettibone | A01G 31/042 47/65 |
| 2011/0131876 A1* | 6/2011 | Pettibone | A01G 31/042 47/65 |
| 2012/0017507 A1* | 1/2012 | Owens, Jr. | A01G 9/143 47/1.01 P |
| 2012/0054061 A1* | 3/2012 | Fok | A01G 13/0268 705/26.5 |
| 2013/0104453 A1* | 5/2013 | Hassle | A01C 1/02 47/17 |
| 2013/0104454 A1* | 5/2013 | Deppermann | A01G 22/00 47/58.1 R |
| 2014/0242681 A1* | 8/2014 | Fiorentino | C12N 1/12 435/287.1 |
| 2014/0259920 A1* | 9/2014 | Wilson | A01C 1/00 47/62 R |
| 2014/0325910 A1 | 11/2014 | Faris | |
| 2015/0250115 A1* | 9/2015 | Pickell | A01G 31/042 47/62 R |
| 2016/0026940 A1* | 1/2016 | Johnson | A01B 79/005 705/7.11 |
| 2016/0192594 A1* | 7/2016 | Mawendra | A01G 31/042 47/62 R |
| 2016/0192607 A1* | 7/2016 | Kitagawa | A01G 9/143 47/62 E |
| 2016/0215994 A1* | 7/2016 | Mewes | G06Q 50/02 |
| 2016/0283791 A1* | 9/2016 | Ogura | G06T 3/4015 |
| 2016/0302369 A1* | 10/2016 | Pickell | A01G 31/045 |
| 2017/0042095 A1* | 2/2017 | Van De Vegte | A01G 18/70 |
| 2017/0142912 A1* | 5/2017 | Gasmer | A01G 9/025 |
| 2017/0172117 A1* | 6/2017 | De Meester | A01K 67/02 |
| 2017/0325398 A1* | 11/2017 | Heinrich | A01C 21/007 |
| 2017/0339846 A1* | 11/2017 | Lawrence | A01G 9/088 |
| 2018/0014452 A1* | 1/2018 | Starr | A01G 7/00 |
| 2018/0059691 A1* | 3/2018 | Fleming | G06Q 50/02 |
| 2018/0206422 A1* | 7/2018 | Vandecruys | A01G 31/06 |
| 2018/0271029 A1* | 9/2018 | Hatamian | G06K 9/6202 |
| 2018/0276504 A1* | 9/2018 | Yamaguchi | G06K 9/3241 |
| 2019/0216020 A1* | 7/2019 | Simske | A01G 7/00 |
| 2019/0327913 A1* | 10/2019 | Chong | A01G 9/249 |
| 2019/0387223 A1* | 12/2019 | Uejima | A01G 7/00 |
| 2020/0100445 A1* | 4/2020 | Saba | G06F 7/00 |
| 2020/0104988 A1* | 4/2020 | Baurer | G06F 16/5866 |
| 2020/0154646 A1* | 5/2020 | Johnson | A01G 25/09 |
| 2020/0333782 A1* | 10/2020 | Kent | G05D 1/0022 |
| 2020/0359569 A1* | 11/2020 | McNamara | A01G 9/16 |
| 2020/0359570 A1* | 11/2020 | Portello | A01G 22/00 |
| 2020/0367455 A1* | 11/2020 | Vesty | A01G 31/042 |

FOREIGN PATENT DOCUMENTS

| | | |
|---|---|---|
| KR | 20160131522 A | 11/2016 |
| KR | 101783212 B1 | 9/2017 |
| WO | 9305643 A1 | 4/1993 |
| WO | 2011125965 A1 | 10/2011 |
| WO | 2017131207 A1 | 8/2017 |

\* cited by examiner

SYSTEMS AND METHODS FOR BYPASSING HARVESTING FOR A GROW POD

CROSS REFERENCE TO RELATED APPLICATIONS

This application claims the benefit of U.S. Provisional Patent Application Nos. 62/519,661, 62/519,665 and 62/519,304 all filed on Jun. 14, 2017, the entire contents of which are herein incorporated by reference.

TECHNICAL FIELD

Embodiments described herein generally relate to systems and methods for bypassing harvesting plants in a grow pod and, more specifically, to bypassing harvesting plants in a grow pod and extending the period of growth of the plants based on the status of the plants.

BACKGROUND

While crop growth technologies have advanced over the years, there are still many problems in the farming and crop industry today. As an example, while technological advances have increased efficiency and production of various crops, many factors may affect a harvest, such as weather, disease, infestation, and the like. Additionally, while the United States currently has suitable farmland to adequately provide food for the U.S. population, other countries and future populations may not have enough farmland to provide the appropriate amount of food.

Growth of plants may be varied depending on growing conditions. Some plants may not be sufficiently grown before being harvested in an automated harvesting system. Thus, a system for bypassing harvesting plants and selectively providing extended period of growth may be needed.

SUMMARY

In one embodiment, a system for bypassing harvesting in an assembly line grow pod is provided. The system includes a track, a cart configured to move on the track, the cart including an upper plate configured to support a plant, one or more sensors and a controller. The controller includes one or more processors, one or more memory modules, and machine readable instructions stored in the one or more memory modules that, when executed by the one or more processors, cause the controller to: receive information about the plant from the one or more sensors, determine whether the plant in the cart is ready to harvest based on the information; and transmit an instruction for bypassing harvesting the plant in the cart in response to determination that the plant in the cart is not ready to harvest.

In another embodiment, a controller for bypassing harvesting a plant in a cart is provided. The controller includes one or more processors, one or more memory modules, and machine readable instructions stored in the one or more memory modules. The machine readable instructions, when executed by the one or more processors, cause the controller to: sending, to the cart, an instruction for moving on a track, receive information about the plant in the cart from one or more sensors, determine whether the plant in the cart is ready to harvest based on the information and transmit an instruction for bypassing harvesting the plant in the cart in response to determination that the plant in the cart is not ready to harvest.

In another embodiment, a method for bypassing harvesting a plant in a cart is provided. The method includes sending, to the cart, an instruction for moving on a track, receiving information about the plant in the cart from one or more sensors, determining whether the plant in the cart is ready to harvest based on the information, and transmitting an instruction for bypassing harvesting the plant in the cart in response to determination that the plant in the cart is not ready to harvest.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the disclosure. The following detailed description of the illustrative embodiments can be understood when read in conjunction with the following drawings, where like structure is indicated with like reference numerals and in which.

DETAILED DESCRIPTION

Embodiments disclosed herein include systems for bypassing harvesting. The system includes a track, a cart configured to move on the track, the cart including an upper plate configured to support a plant, one or more sensors and a controller. The controller includes one or more processors, one or more memory modules, and machine readable instructions stored in the one or more memory modules that, when executed by the one or more processors, cause the controller to: receive information about the plant from the one or more sensors, determine whether the plant in the cart is ready to harvest based on the information; and transmit an instruction for bypassing harvesting the plant in the cart in response to determination that the plant in the cart is not ready to harvest. The track may include a primary track, and a secondary track connected to the primary track. The controller may transmit an instruction for switching a path of the cart from the primary track to the secondary track in response to determination that the plant in the cart is not ready to harvest. The system according to the present disclosure bypasses harvesting plants and selectively provided extended period of growth for the plants. As such, every plant may be fully grown before being harvested in an assembly line grow pod.

Figure 1:
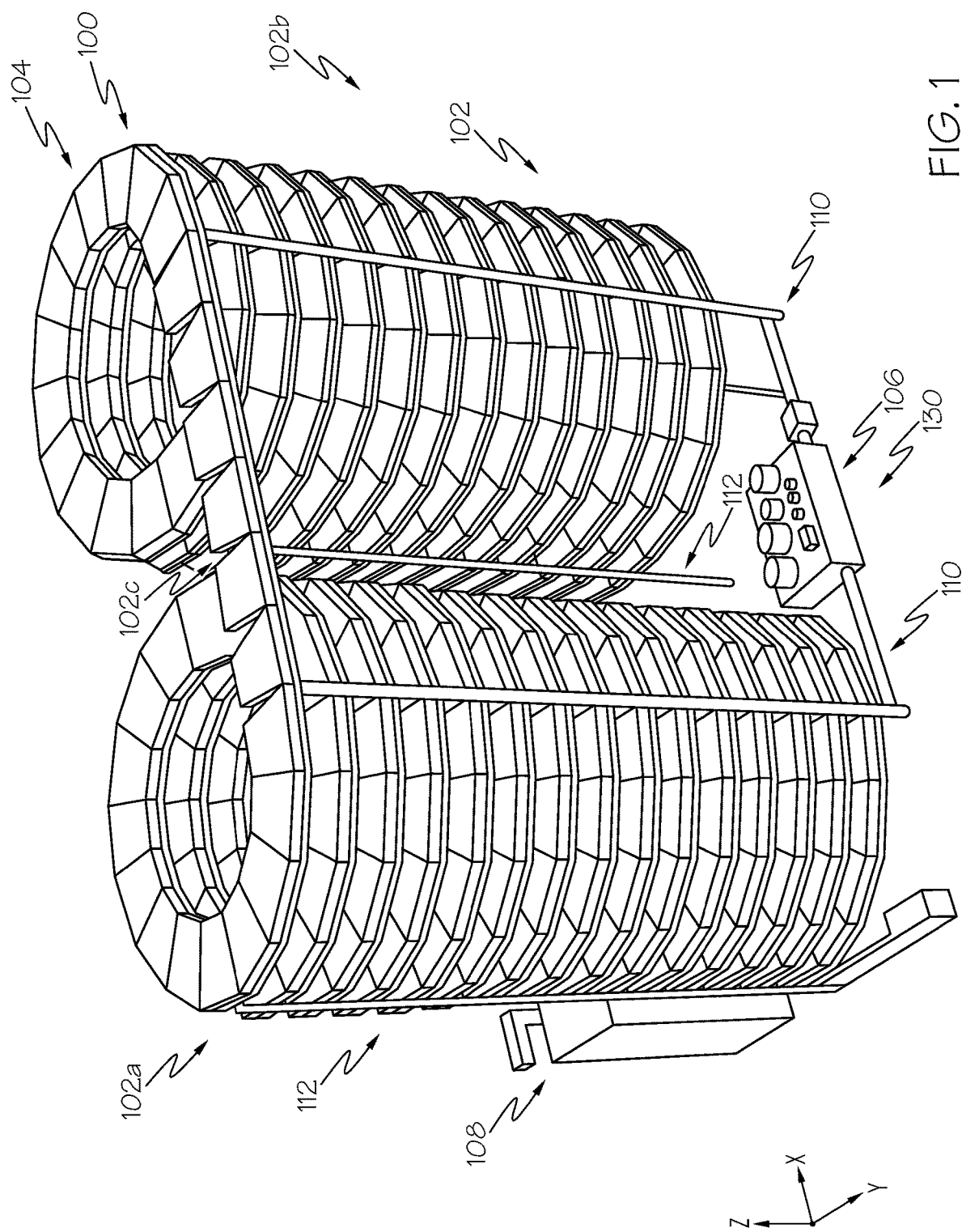
FIG. 1 depicts an assembly line grow pod, according to embodiments described herein.

Referring now to the drawings, FIG. 1 depicts an assembly line grow pod 100 that receives a plurality of industrial carts 104, according to embodiments described herein. The assembly line grow pod 100 may be positioned on an x-y plane as shown in FIG. 1. As illustrated, the assembly line grow pod 100 may include a track 102 that holds one or more industrial carts 104. Each of the one or more industrial carts 104, as described in more detail with reference to FIG. 2, may include one or more wheels 222a, 222b, 222c, and 222d rotatably coupled to the industrial cart 104 and supported on the track 102, as described in more detail with reference to FIG. 2.

Additionally, a drive motor is coupled to the industrial cart 104. In some embodiments, the drive motor may be coupled to at least one of the one or more wheels 222a, 222b, 222c, and 222d such that the industrial cart 104 may be propelled along the track 102 in response to a signal transmitted to the drive motor. In other embodiments, the drive motor may be rotatably coupled to the track 102. For example, the drive motor may be rotatably coupled to the track 102 through one or more gears which engage a plurality of teeth arranged along the track 102 such that the industrial cart 104 may be propelled along the track 102.

The track 102 may include a plurality of modular track sections. The plurality of modular track sections may include a plurality of straight modular track sections and a plurality of curved modular track sections. The track 102 may include an ascending portion 102a, a descending portion 102b, and a connection portion 102c. The ascending portion 102a and the descending portion 102b may include the plurality of curved modular track sections. The ascending portion 102a may wrap around (e.g., in a counterclockwise direction as depicted in FIG. 1) a first axis such that the industrial carts 104 ascend upward in a vertical direction. The first axis may be parallel to the z axis as shown in FIG. 1 (i.e., perpendicular to the x-y plane).

The descending portion 102b may be wrapped around a second axis (e.g., in a counterclockwise direction as depicted in FIG. 1) that is substantially parallel to the first axis, such that the industrial carts 104 may be returned closer to ground level. The plurality of curved modular track sections of the descending portion 102b may be tilted relative to the x-y plane (i.e., the ground) by a predetermined angle.

The connection portion 102c may include a plurality of straight modular track sections. The connection portion 102c may be relatively level with respect to the x-y plane (although this is not a requirement) and is utilized to transfer the industrial carts 104 from the ascending portion 102a to the descending portion 102b. In some embodiments, a second connection portion (not shown in FIG. 1) may be positioned near ground level that couples the descending portion 102b to the ascending portion 102a such that the industrial carts 104 may be transferred from the descending portion 102b to the ascending portion 102a. The second connection portion may include a plurality of straight modular track sections.

In some embodiments, the track 102 may include two or more parallel rails that support the industrial cart 104 via the one or more wheels 222a, 222b, 222c, and 222d rotatably coupled thereto. In some embodiments, at least two of the parallel rails of the track 102 are electrically conductive, thus capable of transmitting communication signals and/or power to and from the industrial cart 104. In some embodiments, a portion of the track 102 is electrically conductive and a portion of the one or more wheels 222a, 222b, 222c, and 222d are in electrical contact with the portion of the track 102 which is electrically conductive. In some embodiments, the track 102 may be segmented into more than one electrical circuit. That is, the electrically conductive portion of the track 102 may be segmented with a non-conductive section such that a first electrically conductive portion of the track 102 is electrically isolated from a second electrically conductive portion of the track 102 which is adjacent to the first electrically conductive portion of the track 102.

The communication signals and power may further be received and/or transmitted via the one or more wheels 222a, 222b, 222c, and 222d of the industrial cart 104 and to and from various components of industrial cart 104, as described in more detail herein. Various components of the industrial cart 104, as described in more detail herein, may include the drive motor, the control device, and one or more sensors.

In some embodiments, the communication signals and power signals may include an encoded address specific to an industrial cart 104 and each industrial cart 104 may include a unique address such that multiple communication signals and power may be transmitted over the same track 102 and received and/or executed by their intended recipient. For example, the assembly line grow pod 100 system may implement a digital command control system (DCC). DDC systems encode a digital packet having a command and an address of an intended recipient, for example, in the form of a pulse width modulated signal that is transmitted along with power to the track 102.

In such a system, each industrial cart 104 includes a decoder, which may be the control device coupled to the industrial cart 104, designated with a unique address. When the decoder receives a digital packet corresponding to its unique address, the decoder executes the embedded command. In some embodiments, the industrial cart 104 may also include an encoder, which may be the control device coupled to the industrial cart 104, for generating and transmitting communications signals from the industrial cart 104, thereby enabling the industrial cart 104 to communicate with other industrial carts 104 positioned along the track 102 and/or other systems or computing devices communicatively coupled with the track 102.

While the implementation of a DCC system is disclosed herein as an example of providing communication signals along with power to a designated recipient along a common interface (e.g., the track 102) any system and method capable of transmitting communication signals along with power to and from a specified recipient may be implemented. In some embodiments, digital data may be transmitted over AC circuits by utilizing a zero-cross, step, and/or other communication protocol.

While not explicitly illustrated in FIG. 1, the assembly line grow pod 100 may also include a harvesting component, a tray washing component, and other systems and components coupled to and/or in-line with the track 102. In some embodiments, the assembly line grow pod 100 may include a plurality of lighting devices, such as light emitting diodes (LEDs). The lighting devices may be disposed on the track 102 opposite the industrial carts 104, such that the lighting devices direct light waves to the industrial carts 104 on the portion the track 102 directly below. In some embodiments, the lighting devices are configured to create a plurality of different colors and/or wavelengths of light, depending on the application, the type of plant being grown, and/or other factors. Each of the plurality of lighting devices may include a unique address such that a master controller 106 may communicate with each of the plurality of lighting devices. While in some embodiments, LEDs are utilized for this purpose, this is not a requirement. Any lighting device that produces low heat and provides the desired functionality may be utilized.

Also depicted in FIG. 1 is a master controller 106. The master controller 106 may include a computing device 130, a nutrient dosing component, a water distribution component, and/or other hardware for controlling various components of the assembly line grow pod 100. In some embodiments, the master controller 106 and/or the computing device 130 are communicatively coupled to a network 620 (as depicted and further described with reference to FIG. 6).

Coupled to the master controller 106 is a seeder component 108. The seeder component 108 may be configured to seed one or more industrial carts 104 as the industrial carts 104 pass the seeder in the assembly line. Depending on the particular embodiment, each industrial cart 104 may include a single section tray for receiving a plurality of seeds. Some embodiments may include a multiple section tray for receiving individual seeds in each section (or cell). In the embodiments with a single section tray, the seeder component 108 may detect presence of the respective industrial cart 104 and may begin laying seed across an area of the single section tray. The seed may be laid out according to a desired depth of seed, a desired number of seeds, a desired surface area of seeds, and/or according to other criteria. In some embodiments, the seeds may be pre-treated with nutrients and/or anti-buoyancy agents (such as water) as these embodiments may not utilize soil to grow the seeds and thus might need to be submerged.

In the embodiments where a multiple section tray is utilized with one or more of the industrial carts 104, the seeder component 108 may be configured to individually insert seeds into one or more of the sections of the tray. Again, the seeds may be distributed on the tray (or into individual cells) according to a desired number of seeds, a desired area the seeds should cover, a desired depth of seeds, etc. In some embodiments, the seeder component 108 may communicate the identification of the seeds being distributed to the master controller 106.

The watering component may be coupled to one or more water lines 110, which distribute water and/or nutrients to one or more trays at predetermined areas of the assembly line grow pod 100. In some embodiments, seeds may be sprayed to reduce buoyancy and then flooded. Additionally, water usage and consumption may be monitored, such that at subsequent watering stations, this data may be utilized to determine an amount of water to apply to a seed at that time.

Also depicted in FIG. 1 are airflow lines 112. Specifically, the master controller 106 may include and/or be coupled to one or more components that delivers airflow for temperature control, humidity control, pressure control, carbon dioxide control, oxygen control, nitrogen control, etc. Accordingly, the airflow lines 112 may distribute the airflow at predetermined areas in the assembly line grow pod 100. For example, the airflow lines 112 may extend to each story of the ascending portion 102a and the descending portion 102b.

It should be understood that while some embodiments of the track may be configured for use with a grow pod, such as that depicted in FIG. 1, this is merely an example. The track and track communications are not so limited and can be utilized for any track system where communication is desired.

Figure 2:
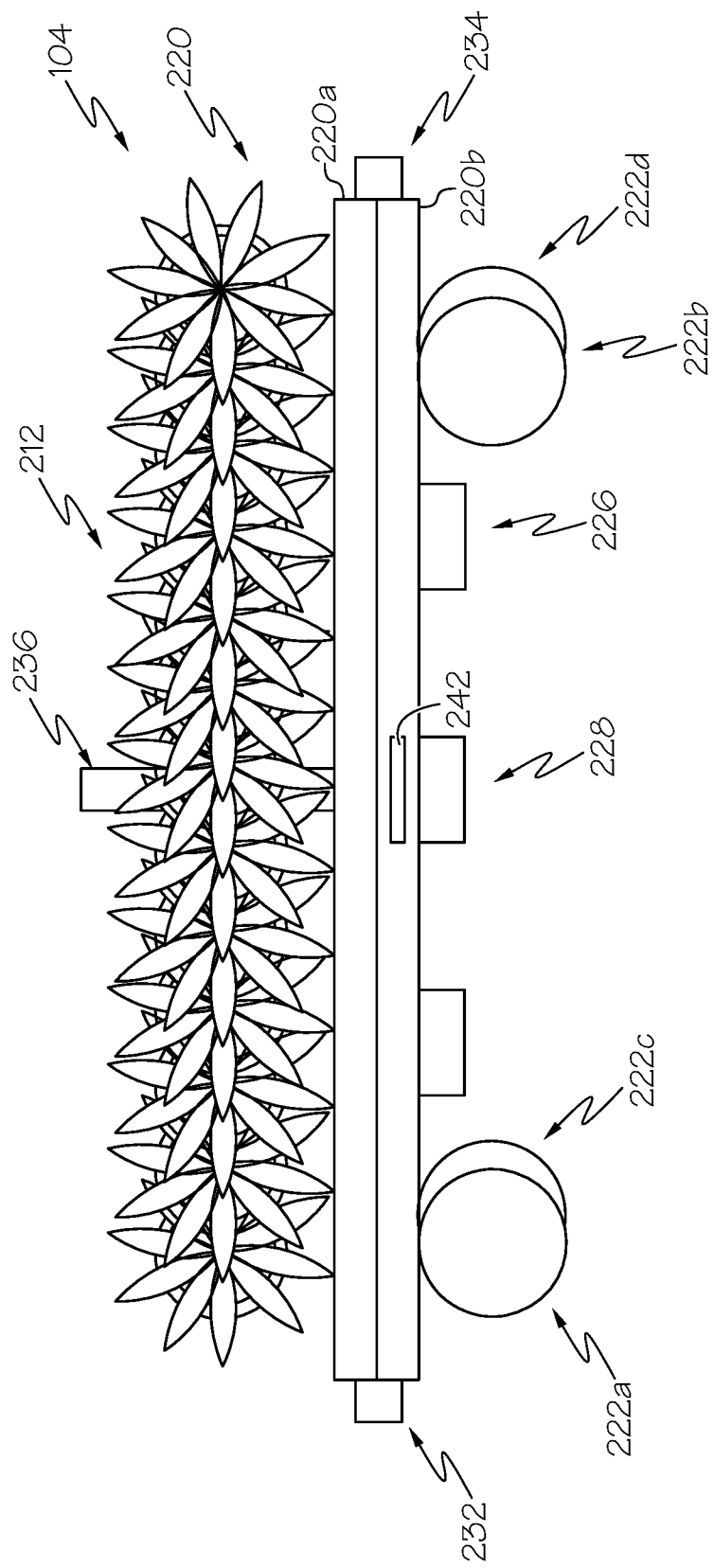
FIG. 2 depicts an industrial cart, according to embodiments described herein.

FIG. 2 depicts an industrial cart 104 that may be utilized for the assembly line grow pod 100, according to embodiments described herein. As illustrated, the industrial cart 104 includes a tray section 220 and one or more wheels 222a, 222b, 222c, and 222d. The tray section 220 includes an upper plate 220a and a lower plate 220b. The one or more wheels 222a, 222b, 222c, and 222d may be configured to rotatably couple with the track 102, as well as receive power, from the track 102. The track 102 may additionally be configured to facilitate communication with the industrial cart 104 through the one or more wheels 222a, 222b, 222c, and 222d.

In some embodiments, one or more components may be coupled to the tray section 220. For example, a drive motor 226, a cart computing device 228, and/or a payload 212 may be coupled to the tray section 220 of the industrial cart 104. The tray section 220 may additionally include a payload 212. Depending on the particular embodiment, the payload 212 may be configured as plants (such as in an assembly line grow pod 100); however this is not a requirement, as any payload 212 may be utilized.

The drive motor 226 may be configured as an electric motor and/or any device capable of propelling the industrial cart 104 along the track 102. For example, the drive motor 226 may be configured as a stepper motor, an alternating current (AC) or direct current (DC) brushless motor, a DC brushed motor, or the like. In some embodiments, the drive motor 226 may comprise electronic circuitry which may adjust the operation of the drive motor 226 in response to a communication signal (e.g., a command or control signal) transmitted to and received by the drive motor 226. The drive motor 226 may be coupled to the tray section 220 of the industrial cart 104 or directly coupled to the industrial cart 104.

In some embodiments, the cart computing device 228 may control the drive motor 226 in response to a leading sensor 232, a trailing sensor 234, and/or an orthogonal sensor 236 included on the industrial cart 104. Each of the leading sensor 232, the trailing sensor 234, and the orthogonal sensor 236 may comprise an infrared sensor, visual light sensor, an ultrasonic sensor, a pressure sensor, a proximity sensor, a motion sensor, a contact sensor, an image sensor, an inductive sensor (e.g., a magnetometer) or other type of sensor. The industrial cart 104 further comprises a weight sensor 242 configured to measure the payload 212 on the industrial cart 104.

Figure 6:
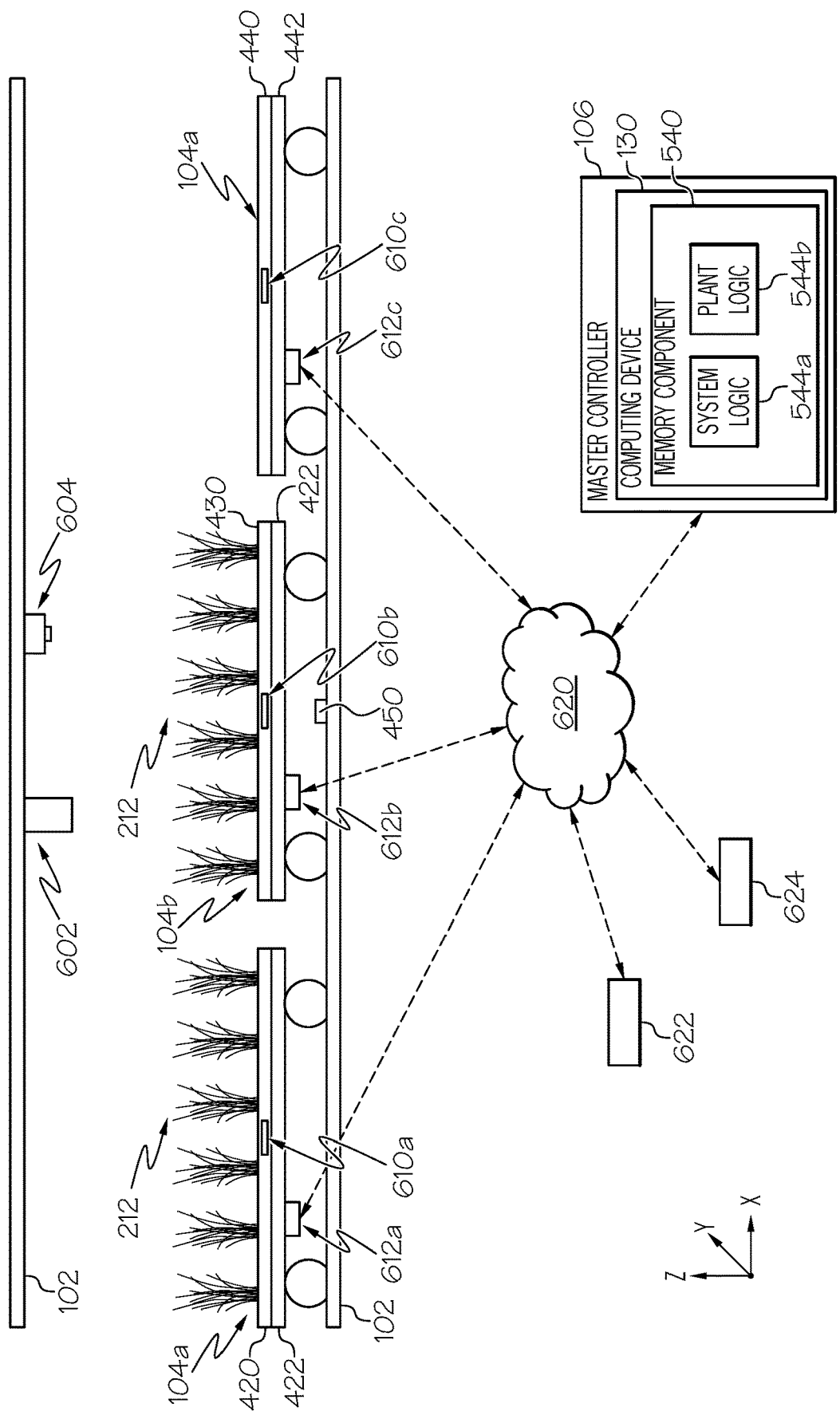
FIG. 6 depict a harvesting system, according to embodiments described herein.

In some embodiments, the leading sensor 232, the trailing sensor 234, the orthogonal sensor 236 and/or the weight sensor 242 may be communicatively coupled to the master controller 106 (FIG. 1). In some embodiments, the leading sensor 232, the trailing sensor 234, the orthogonal sensor 236 and/or the weight sensor 242 may generate one or more signals that may be transmitted via the one or more wheels 222a, 222b, 222c, and 222d and the track 102 (FIG. 1). Similarly, some embodiments may be configured with the track 102 and/or the industrial cart 104 communicatively coupled to a network 620 (FIG. 6). Therefore, the one or more signals may be transmitted to the master controller 106 via the network 550 over network interface hardware 934 (FIG. 11) or the track 102 and in response, the master controller 106 may return a control signal to the drive motor 226 for controlling the operation of one or more drive motors 226 of one or more industrial carts 104 positioned on the track 102.

Figure 11:
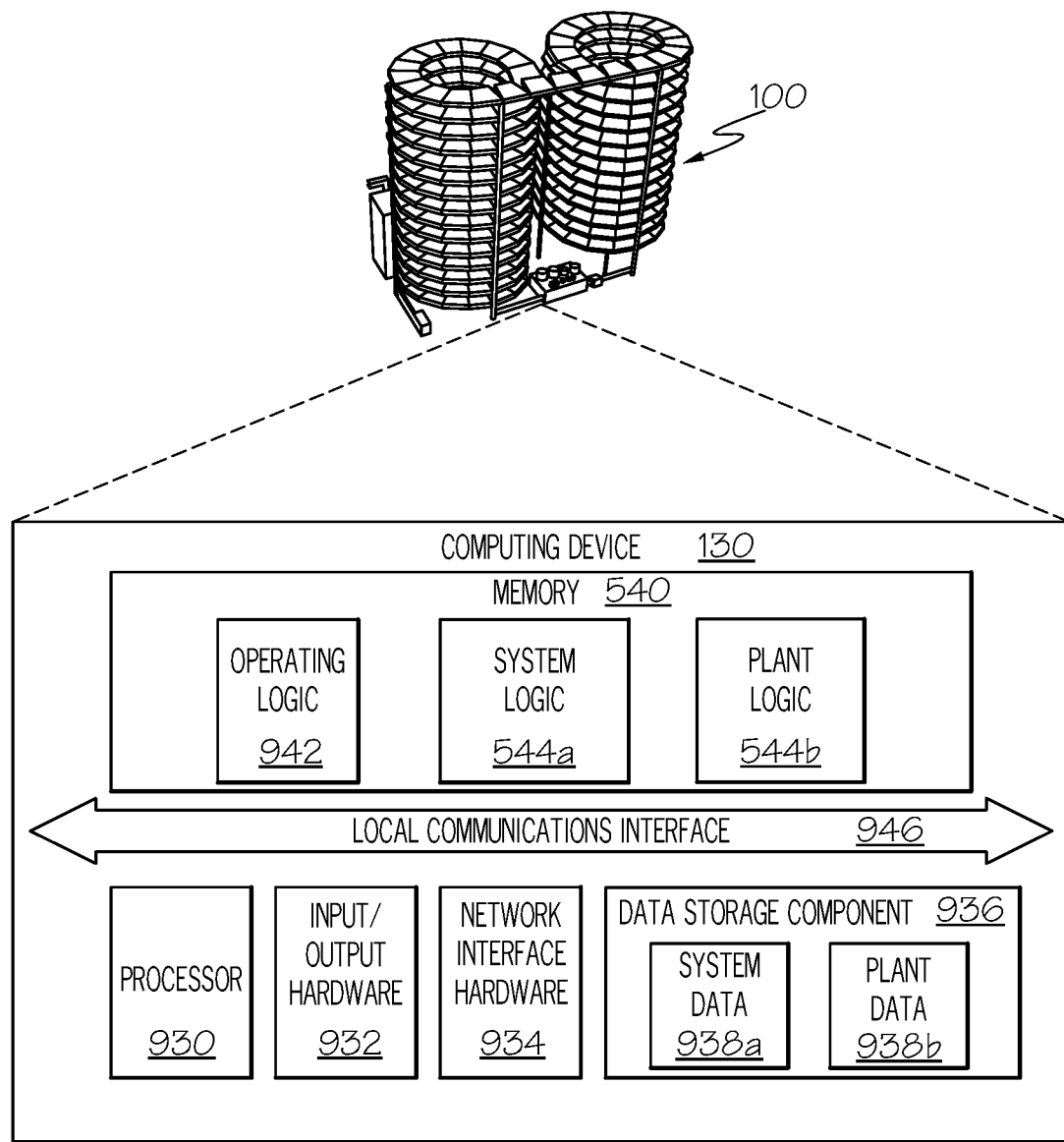
FIG. 11 depicts a computing device for an assembly line grow pod, according to embodiments described herein.

In some embodiments, location markers 224 may be placed along the track 102 or the supporting structures to the track 102 at pre-defined intervals. The orthogonal sensor 236, for example, comprises a photo-eye type sensor and may be coupled to the industrial cart 104 such that the photo-eye type sensor may view the location markers 224 positioned along the track 102 below the industrial cart 104. As such, the cart computing device 228 and/or master controller 106 may receive one or more signals generated from the photo-eye in response to detecting a location marker 224 as the industrial cart travels along the track 102. The cart computing device 228 and/or master controller 106, from the one or more signals, may determine the speed of the industrial cart 104. The speed information may be transmitted to the master controller 106 via the network 620 over network interface hardware 634 (FIG. 11).

Figure 3A:
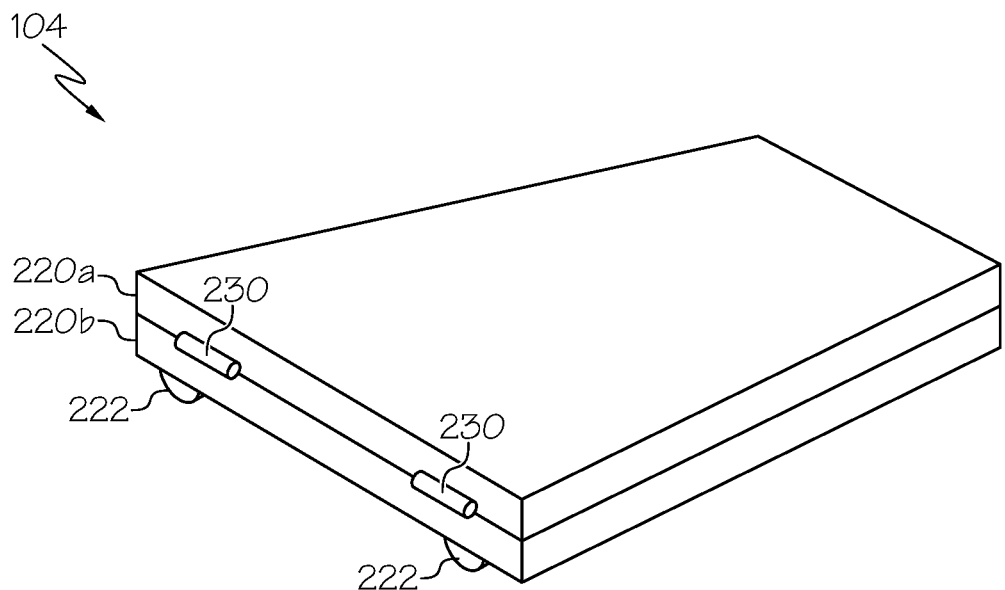
FIG. 3A depicts an industrial cart in a normal mode, according to embodiments described herein.
Figure 3B:
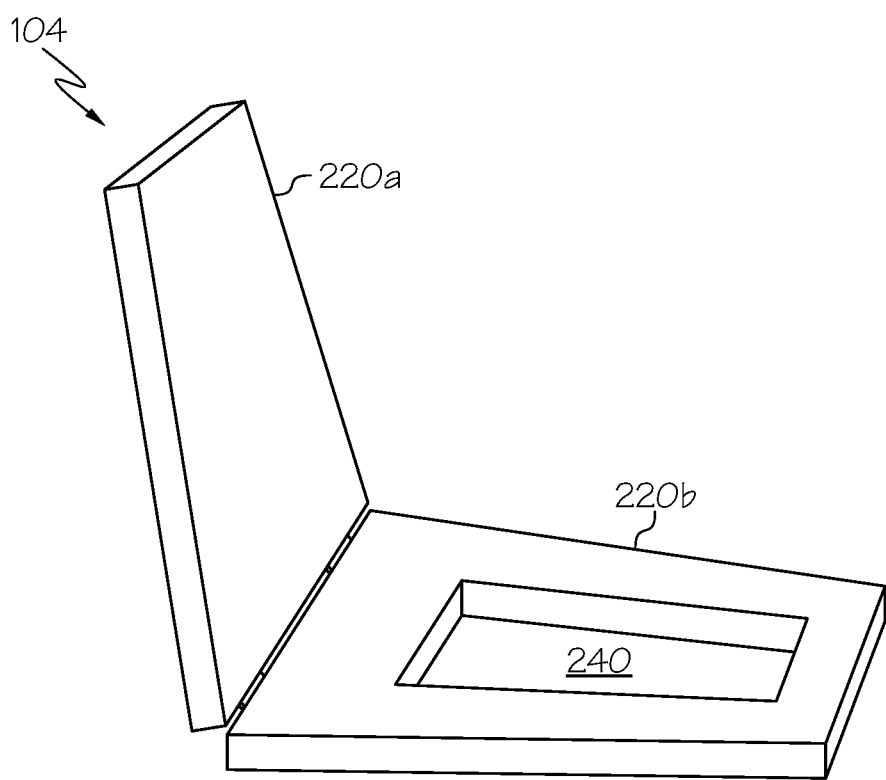
FIG. 3B depicts an industrial cart in a harvest mode, according to embodiments described herein.

FIGS. 3A and 3B depict an operation of the tray of the industrial cart 104 that may be utilized for the assembly line grow pod 100, according to embodiments described herein. The industrial cart 104 includes an upper plate 220a, a lower plate 220b, and one or more wheels 222 as shown in FIG. 2. The upper plate 220a is pivotally coupled to the lower plate 220b via one or more hinges 230. FIG. 3A depicts the industrial cart 104 in a normal mode moving on the track 102. FIG. 3B depicts the industrial cart 104 in a harvesting mode. During the harvesting mode, the upper plate 220a is pivotally rotated against the lower plate 220b such that payload on the upper plate 220a may be dumped out from the industrial cart 104. As depicted in FIG. 3B, the lower plate 220b includes an opening 240 that allows a lifter 450 (FIG. 4) to move through.

Figure 4:
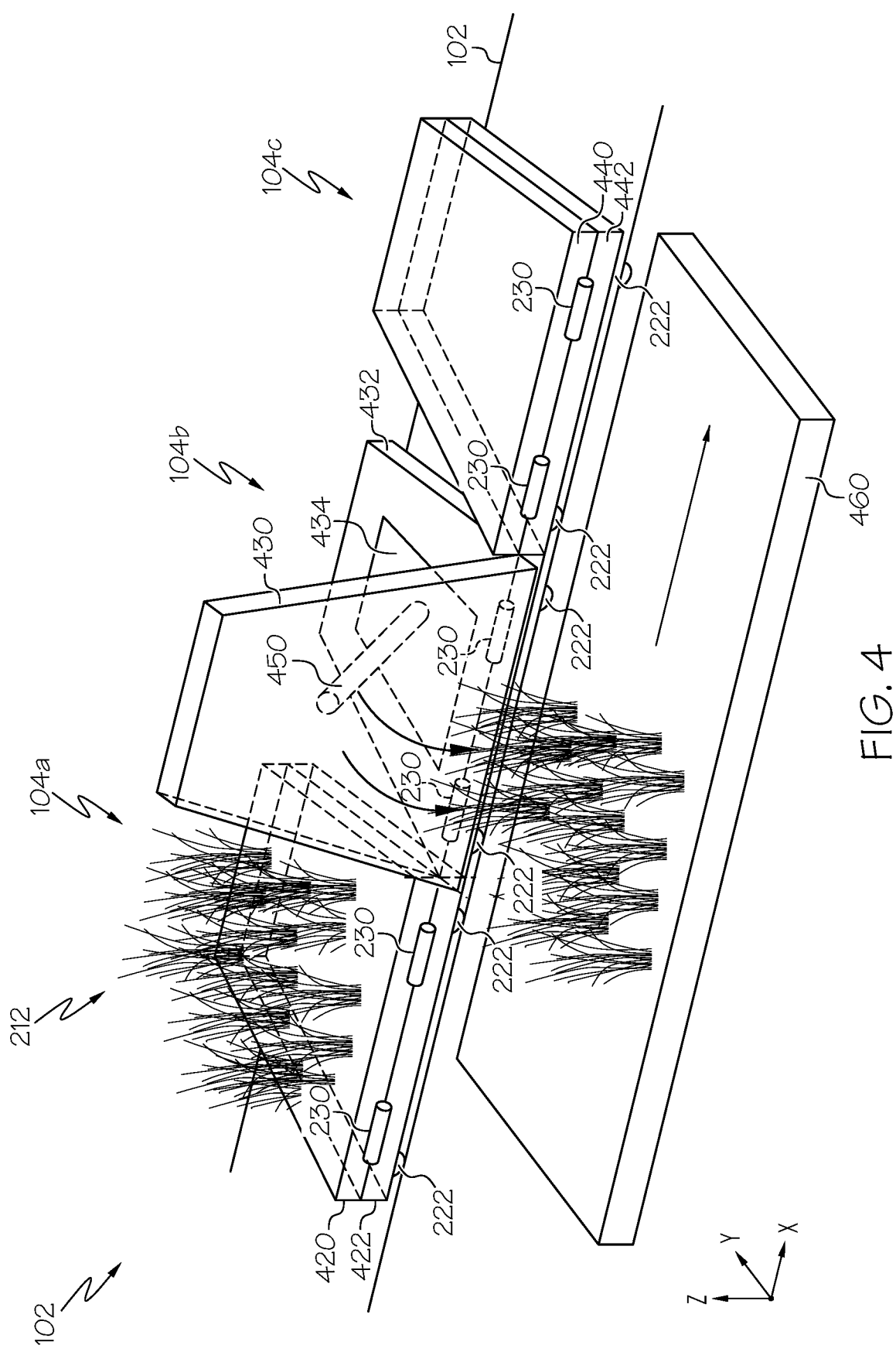
FIG. 4 depicts harvesting plant on an industrial cart, according to embodiments described herein.

FIG. 4 depicts harvesting operation of industrial carts, according to embodiments shown and described herein. As illustrated, industrial carts 104a, 104b, and 104c are disposed on a track 102. Each of the industrial carts 104a, 104b, and 104c is depicted as being similarly configured as the industrial cart 104 from FIG. 2. As discussed above, at least a portion of the one or more wheels 222 (or other portion of the industrial carts 104a, 104b, and 104c) may couple with the track 102 to receive communication signals and/or power.

The industrial carts 104a, 104b, and 104c may move along the track 102 in +x direction. That is, the industrial cart 104a will be at the position of the industrial cart 104b shown in FIG. 4 at a certain point of time. In embodiments, the industrial cart 104a operates in a normal mode carrying payload 212, and the industrial cart 104b is in a harvesting mode. The industrial cart 104b may operate in a harvest mode when the industrial cart 104b is determined to be in a harvesting area. For example, the industrial cart 104b may receive a signal from the master controller 106 that the industrial cart 104b is in a harvesting area. In response to receiving the signal indicating that the industrial cart 104b is in the harvesting area, the industrial cart 104b may stop moving in +x direction. As another example, the track 102 may include a harvesting location marker. The industrial cart 104b may read the harvesting location marker using a photo-eye detector, and stop moving in response to reading the harvesting location marker.

A lifter 450 located at the bottom of the industrial cart 104b pushes the upper plate 430 of the industrial cart 104b through an opening 434 in +z direction. The detailed operations of the lifter 450 will be described below with reference to FIGS. 5A through 5C. In response, the upper plate 430 is rotated about the hinges 230 and payload on the industrial cart 104b is dumped out from the industrial cart 104b as indicated by arrows in FIG. 4. The payload on the industrial cart 104b may be dumped to a conveyor belt 460 which transmit the payload to a collecting area. Once the payload is dumped out from the industrial cart 104b, the lifter 450 moves down in −z direction such that the upper plate 430 is placed on the lower plate 422 similar to the industrial cart 104c.

In some embodiments, before the upper plate 430 is pushed up by the lifter 450, the water in the industrial cart 104b may be removed. For example, the industrial cart 104b may include water detection sensors for detecting water in the industrial cart 104b. The master controller 106 may determine that there is water in the industrial cart 104b, and send an instruction for removing water from the industrial cart 104b. For example, the master controller 106 may send an instruction to the lifter 450 to rotate such that the industrial cart 104b is slightly tilted (e.g., by 5 degrees). Then, the water in the industrial cart 104b may gather at the edge of the industrial cart 104b where there is a hole through which the water flows out from the industrial cart 104b. As another example, the master controller 106 may send an instruction to a vacuum robot to remove water from the industrial cart 104b.

Figure 5A:
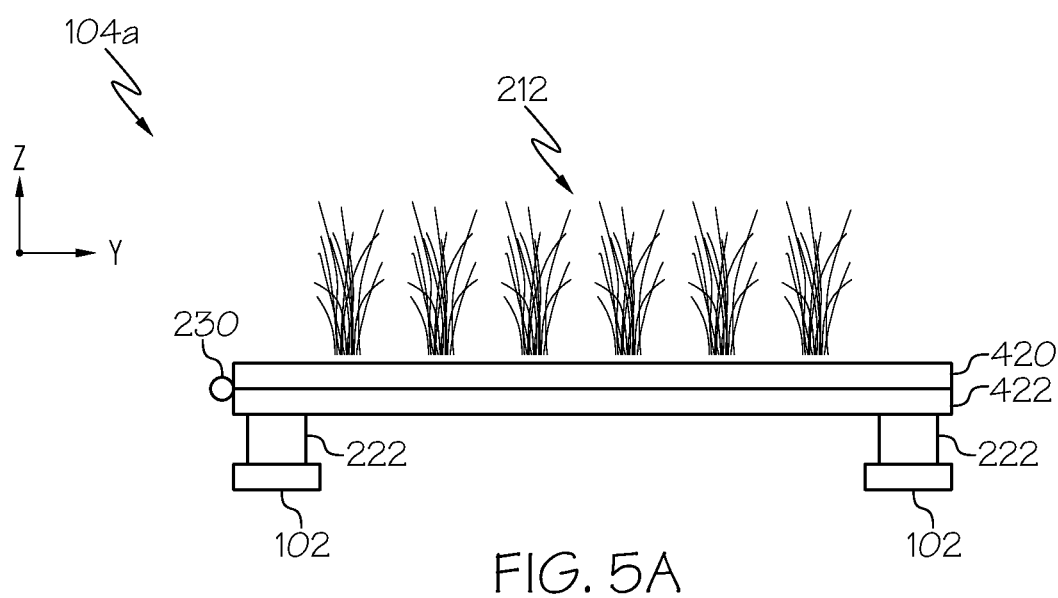
FIG. 5A depicts an industrial cart in a normal mode, according to embodiments described herein.
Figure 5B:
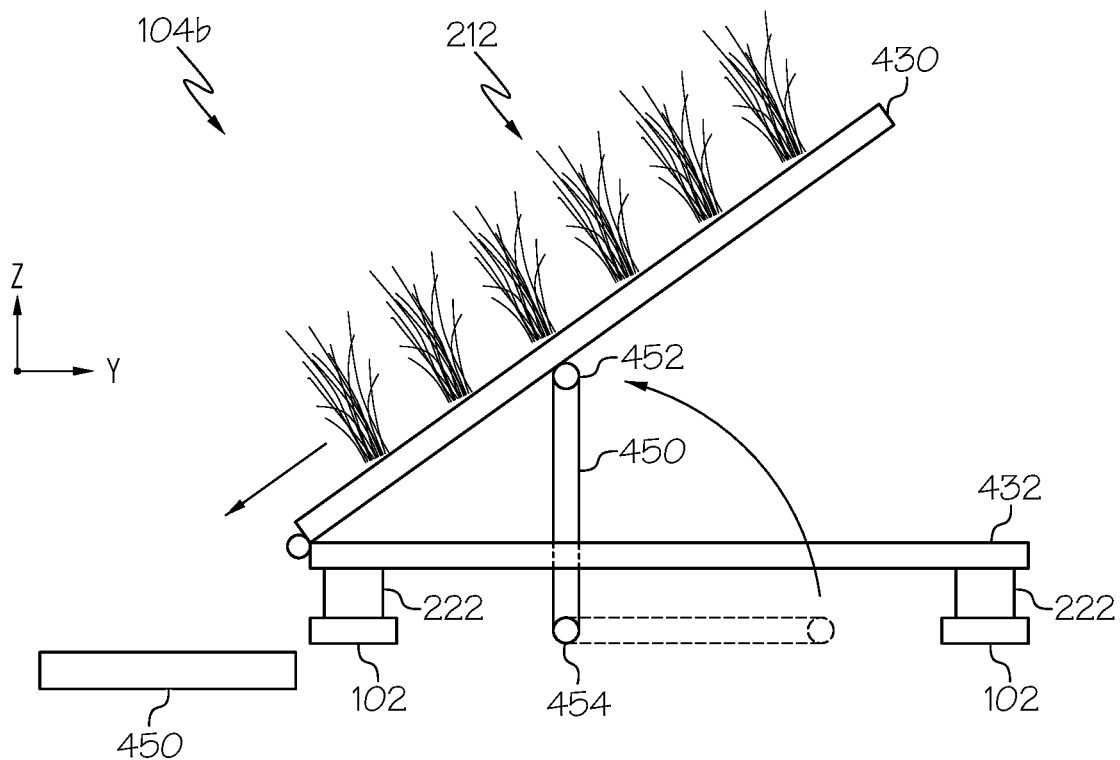
FIG. 5B depicts an industrial cart in a harvest mode, according to embodiments described herein.
Figure 5C:
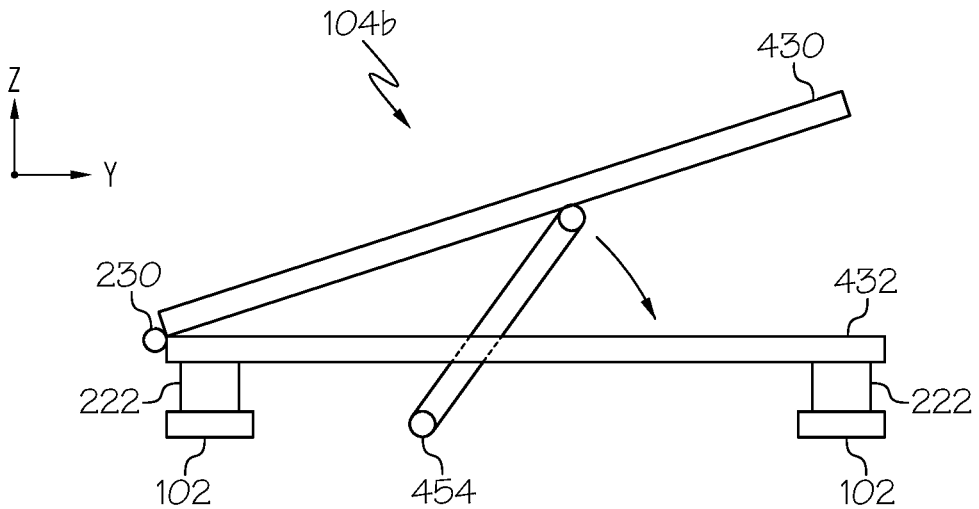
FIG. 5C depicts an industrial cart in a harvest mode, according to embodiments described herein.

FIGS. 5A, 5B, and 5C depict a y-z plane view of the industrial carts shown in FIG. 4, according to one or more embodiments shown and described herein. FIG. 5A depicts a y-z plane view of the industrial cart 104a depicted in FIG. 4. In embodiments, the upper plate 220a is placed on and parallel to the lower plate 220b. The upper plate 220a is coupled to the lower plate 220b via one or more hinges 230. Wheels 222 of the industrial cart 104a are on the track 102 such that the industrial cart 104a moves along the track 102.

FIG. 5B depicts a y-z plane view of the industrial cart 104b depicted in FIG. 4. The industrial cart 104b is in a harvesting mode. The industrial cart 104 stops moving on the track 102. The lifter 450 is configured to rotate about a pivot 454. As shown in FIG. 5B, the original position of the lifter 450 is indicated in broken lines. In embodiments, the lifter 450 may receive an instruction from the master controller 106 to rotate about the pivot 454. In some embodiments, the lifter 450 may receive an instruction from the industrial cart 104b to rotate about the pivot 454. In response to receiving the instruction, the lifter 450 rotates counterclockwise to push up the upper plate 430.

Similarly, the upper plate 430 rotates counterclockwise around the hinge 230 as the lifter 450 pushes the upper plate 430. The payload 212 on the upper plate 430 is dumped out from the upper plate 430 into the conveyor belt 460. While the lifter 450 in FIG. 5B rotates to push upward the upper plate 430, any other operation may be implement to push upward the upper plate 430. For example, the lifter 450 may move +z direction to push the upper plate 430 upward. In embodiments, the payload 212 is hydroponically cultivated and the roots of the payload 212 are intertwined. As such, the entire of the payload 212 may be dumped out of the upper plate 430 at a time. In addition, because the payload 212 had been grown on the cart 104b without any dirt, the harvesting process may be simplified by skipping the process of cleaning out dirt. The lifter 450 includes a wheel 452 rotatably coupled to the lifter 450 such that the wheel 452 smoothly pushes the upper plate 430 by rotating when the lifter 450 is in contact with the upper plate 430 and pushes the upper plate 430.

In embodiments, the lifter 450 pushes the upper plate 430 upward until the upper plate 430 rotates by a certain angel (e.g., 60 degrees). The angle may be predetermined such that payload on the upper plate 430 may slide down or be dumped out from the upper plate 430. In some embodiments, the hinge 230 may prevent the upper plate 430 from rotating more than a certain degrees (e.g., 80 degrees).

FIG. 5C depicts a y-z plane view of the industrial cart 104b depicted in FIG. 4. After the payload 212 is dumped out from the upper plate 430, the lifter 450 is operated to rotate about the pivot 454 clockwise as depicted in FIG. 5C. The upper plate 430 of the industrial cart 104b rotates clockwise as the lifter 450 moves in −z direction. Once the upper plate 430 is placed upon and parallel to the lower plate 432, the industrial cart 104b resumes moving on the track 102. In some embodiments, the industrial cart 104b determines whether the payload 212 was dumped out from the upper plate 430 before resuming moving on the track 102. For example, a weight sensor in the upper plate 430 may measure weight of an object on the upper plate 430. If the measured weight is above a threshold value, the industrial cart 104b may transmit an instruction to the lifter 450 to rotate counterclockwise again in order to dump remaining payload on the upper plate 430.

Figure 5D:
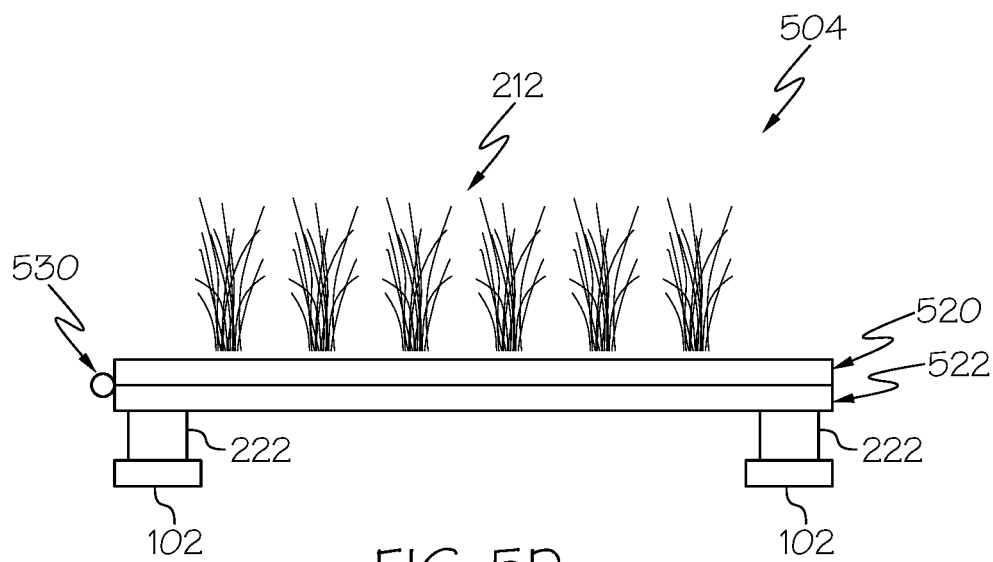
FIG. 5D depicts an industrial cart in a normal mode, according to embodiments described herein.
Figure 5E:
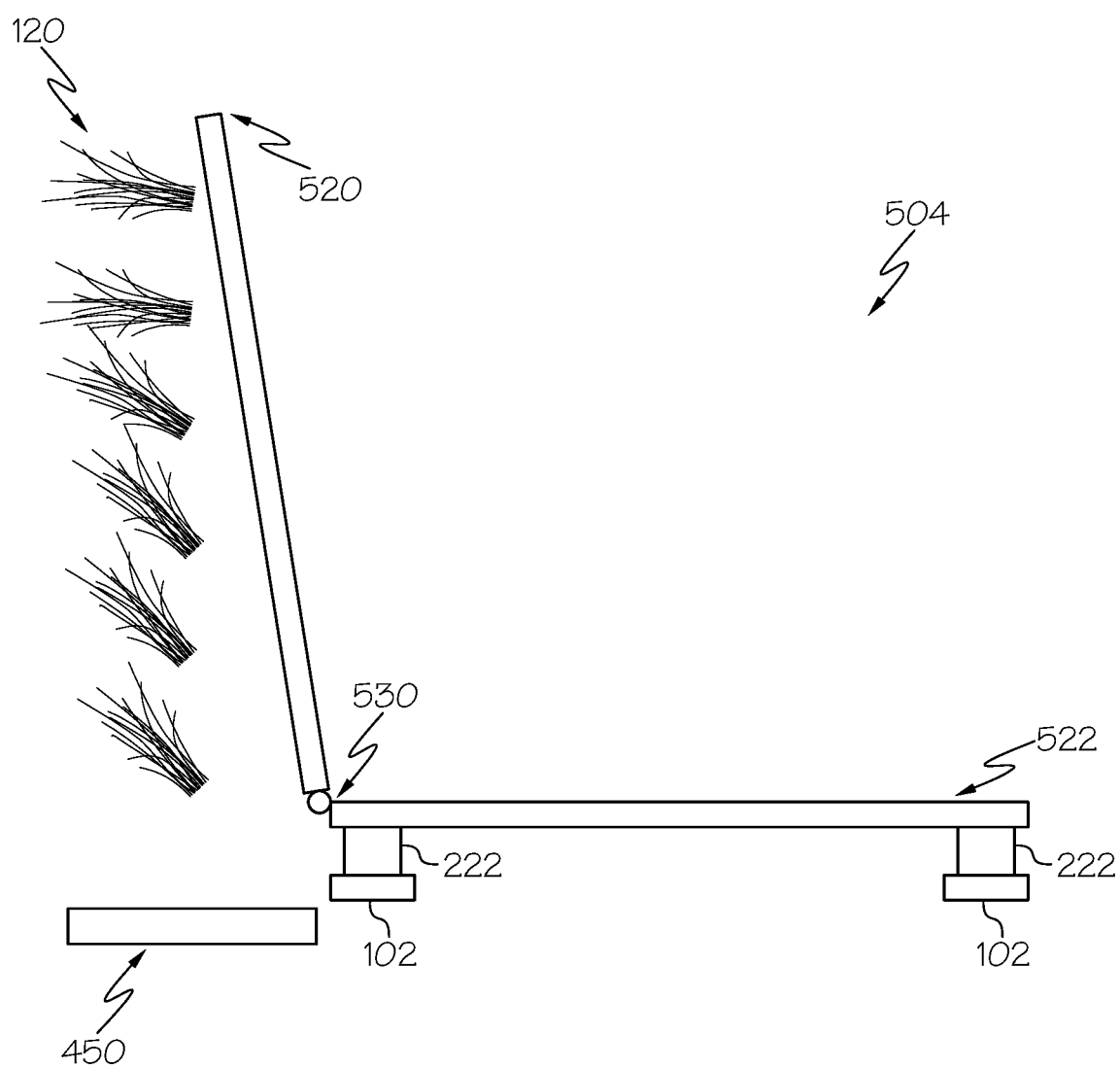
FIG. 5E depicts an industrial cart in a harvest mode, according to embodiments described herein.

FIGS. 5D and 5E depict harvesting plants according another embodiment shown and described herein. As illustrated, the industrial cart 504 is disposed on a track 102. The industrial cart 504 is depicted as being similarly configured as the industrial cart 104 from FIG. 2. The industrial cart 504 includes an upper plate 520 and a lower plate 522. The upper plate 520 is coupled to the lower plate 522 via an actuator 530. The actuator 530 may include an electric motor configured to rotate the upper plate 520 against the lower plate 522. For example, as shown in FIG. 5E, the actuator 530 rotates the upper plate 520 counterclockwise such that the payload 120 is dumped out from the upper plate 520 into the conveyor belt 460. The actuator 530 may rotate the upper plate 520 by a predetermined degree. Once the payload 120 is dumped, the actuator 530 may rotate the upper plate 520 clockwise until the upper plate 520 is placed upon and parallel to the lower plate 522.

FIG. 6 depicts harvesting plants in carts, according to embodiments described herein. Industrial carts 104a, 104b, and 104c move along the track 102 in +x direction through wheels as discussed above with reference to FIG. 4. The industrial cart 104a includes an upper plate 420 and a lower plate 422. The industrial cart 104b includes an upper plate 430 and a lower plate 432. The industrial cart 104c includes an upper plate 440 and a lower plate 442. While the track 102 is illustrated as a straight track in FIG. 6, the track 102 may be a curved track constituting the ascending portion 102a or the descending portion 102b.

In embodiments, the carts 104a, 104b, and 104c include weight sensors 610a, 610b, and 610c, respectively. Each of the weight sensors 610a, 610b, and 610c may be placed in the upper plates 420, 430, and 440 of the carts 104a, 104b, and 104c, respectively. The weight sensors 610a, 610b, and 610c are configured to measure the weight of a payload on the carts, such as plants. The carts 104a, 104b, and 104c also include cart computing devices 612a, 612b, and 612c, respectively. The cart computing devices 612a, 612b, and 612c may be communicatively coupled to the weight sensors 610a, 610b, and 610c and receive weight information from the weight sensors 610a, 610b, and 610c. The cart computing devices 612a, 612b, and 612c may have wireless network interface for communicating with the master controller 106 through a network 620. The master controller 106 may determine whether the measured weight is greater than a threshold weight. The threshold value may be determined based on a plant.

If it is determined that the measured weight is greater than the threshold weight, the master controller 106 may send an instruction to the lifter 450 to rotate as depicted in FIG. 5B to raise the upper plate to dump out payload on the industrial cart, or send an instruction to the actuator 530 in FIG. 5D to rotate the upper plate 520. In some embodiments, each of the carts 104a, 104b, and 104c may include a plurality of weight sensors corresponding to a plurality of cells of the carts 104a, 104b, and 104c. The plurality of weight sensors may determine weights of individual cells or plants on the carts.

In some embodiments, a plurality of weight sensors may be placed on the track 102. The weight sensors are configured to measure the weights of the carts on the track 102 and transmit the weights to the master controller 106. The master controller 106 may determine the weight of payload on a cart by subtracting the weight of the cart from the weight received from the weight sensors on the track 102.

A proximity sensor 602 may be positioned over the carts 104a, 104b, and 104c. In embodiments, the proximity sensor 602 may be attached under the track 102 as depicted in FIG. 6. The proximity sensor 602 may be configured to measure a distance between the proximity sensor 602 and the plants on industrial carts. For example, the proximity sensor 602 may transmit waves and receive waves reflected from the plants. Based on the travelling time of the waves, the proximity sensor 602 may determine the distance between the proximity sensor and the plants. In some embodiments, the proximity sensor 602 may be configured to detect an object within a certain distance. For example, the proximity sensor 602 may detect the plants in the carts 104b if the plants are within 5 inches from the proximity sensor 602. In some embodiments, the proximity sensor 602 may include laser scanners, capacitive displacement sensors, Doppler Effect sensors, eddy-current sensors, ultrasonic sensors, magnetic sensors, optical sensors, radar sensors, sonar sensors, LIDAR sensors or the like. Some embodiments may not include the proximity sensor 602.

The proximity sensor 602 may have wireless network interface for communicating with the master controller 106 through a network 620. In some embodiments, the proximity sensor 602 may communicate with the master controller 106 through wired connection. The master controller 106 may determine the height of payload on the industrial cart based on the measured distance. For example, the master controller 106 calculates the height of payload by subtracting the measured distance from a distance between the proximity sensor 602 and the upper plate 430 of the industrial cart 104b. The master controller 106 may determine whether the calculated height is greater than a threshold height. The threshold height may be determined based on a plant. For example, plant logic 544b of the master controller 106 may store a name of plant and corresponding threshold height.

If it is determined that the calculated height is greater than the threshold height, the master controller 106 may send an instruction to the lifter 450 to rotate as depicted in FIG. 5B to raise the upper plate to dump out payload on the industrial cart. In some embodiments, a plurality of proximity sensors 602 may measure distances between the proximity sensors and the payload, and transmit the distances to the master controller 106. The master controller 106 calculates an average height of the payload based on the received distances from the plurality of proximity sensors 602 and determines whether the average height is greater than the threshold height.

A camera 604 may be positioned over the carts 104a, 104b, and 104c. In embodiments, the camera 604 may be attached under the track 102 as depicted in FIG. 6. The camera 604 may be configured to capture an image of the plants in the cart 104b. The camera 604 may have a wider angle lens to capture plants of more than one carts. For example, the camera 604 may capture the images of payload in the carts 104a, 104b, and 104c. The camera 604 may include a special filter that filters out artificial LED lights from lighting devices in the assembly line grow pod 100 such that the camera 604 may capture the natural colors of the plants.

The camera 604 may transmit the captured image of the payload to the master controller 106. The camera 604 may have wireless network interface for communicating with the master controller 106 through a network 620. In some embodiments, the camera 604 may communicate with the master controller 106 through wired connection. The master controller 106 may determine whether payload is ready to harvest based on the color of the captured image. In embodiments, the master controller 106 may compare the color of the captured image with a threshold color for the identified plant on the industrial cart. The predetermined color for one or more plants may be stored in the plant logic 544b of the master controller 106. For example, the master controller compares RGB levels of the captured image with the RGB levels of the predetermined color, and determines that the plant is ready to harvest based on the comparison.

The master controller 106 may include a computing device 130. The computing device 130 may include a memory component 540, which stores systems logic 544a and plant logic 544b. As described in more detail below, the systems logic 544a may monitor and control operations of one or more of the components of the assembly line grow pod 100. For example, the systems logic 544a may monitor and control operations of the light devices, the water distribution component, the nutrient distribution component, the air distribution component, and harvesting components including the lifter 450. The plant logic 544b may be configured to determine and/or receive a recipe for plant growth and may facilitate implementation of the recipe via the systems logic 544a.

Additionally, the master controller 106 is coupled to a network 620. The network 620 may include the internet or other wide area network, a local network, such as a local area network, a near field network, such as Bluetooth or a near field communication (NFC) network. The network 620 is also coupled to a user computing device 622 and/or a remote computing device 624. The user computing device 622 may include a personal computer, laptop, mobile device, tablet, server, etc. and may be utilized as an interface with a user. As an example, the total weight of plant in each of the industrial carts along with the identification of the industrial cart may be transmitted to the user computing device 622. The average height of a plant in each of the industrial carts may be also transmitted to the user computing device 622. The display of the user computing device 622 may display the weight of plant for each of the carts, as depicted in FIG. 7.

Figure 7:
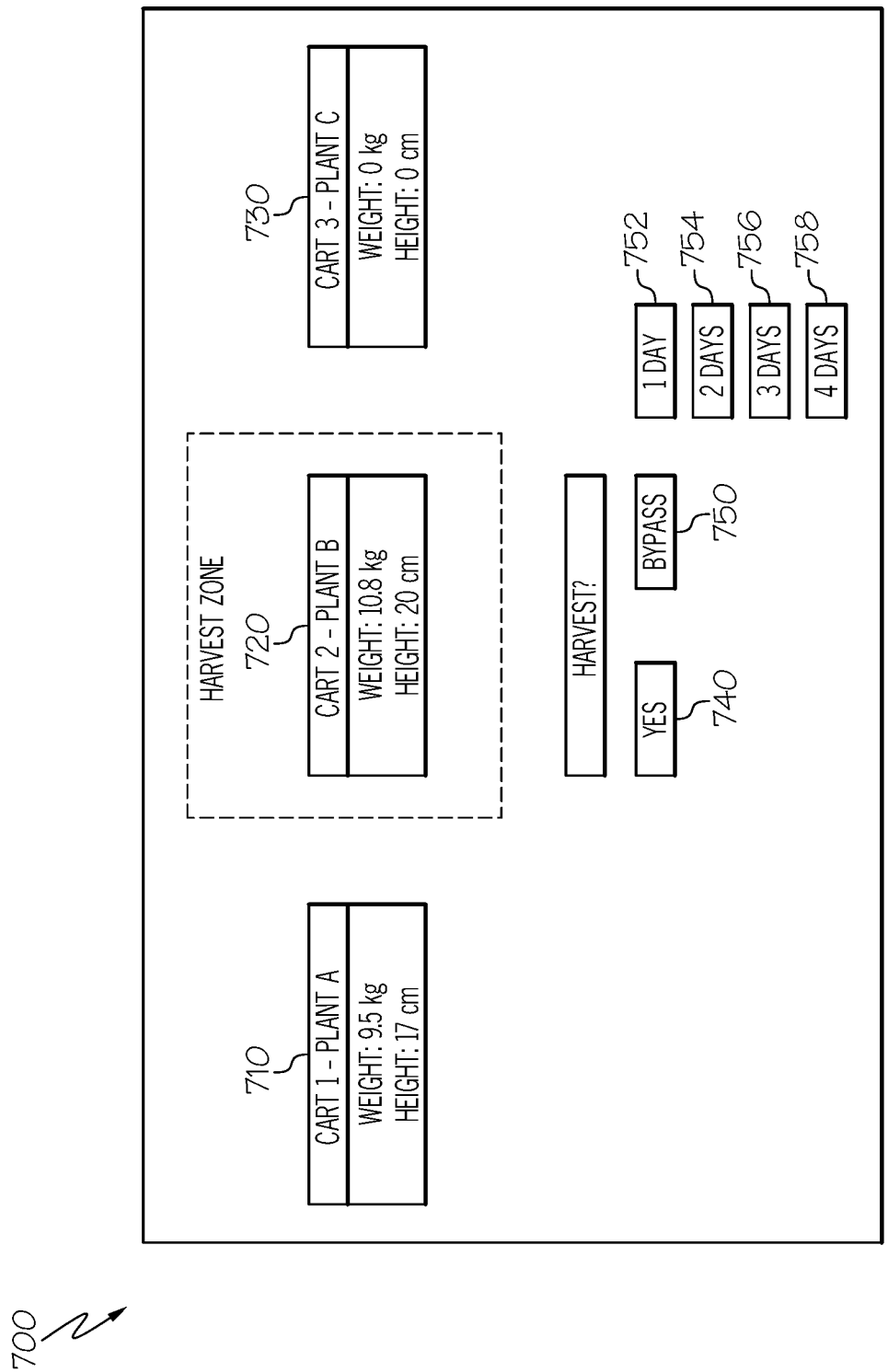
FIG. 7 depicts an interface of a user computing device, according to embodiments described herein.

FIG. 7 depicts a display 700 of the user computing device 622, according to one or more embodiments shown and described herein. In embodiments, the display 700 may display three windows 710, 720, and 730 displaying information about the industrial carts 104a, 104b, and 104c depicted in FIG. 6 respectively. Each of the windows 710, 720, and 730 displays information about plant carried in corresponding industrial cart, the weight of the plant, and the height of the plant. The display 700 may also indicate the industrial cart 104b is in a harvesting zone, and ask whether the plant in the industrial cart 104b is ready to harvest. The harvesting zone may be a zone where the lifter 450 is located, e.g., where the industrial cart 104b in FIG. 4 is located. Additionally, the camera 604 may be positioned above the harvesting zone. In some embodiments, the lighting device above the harvesting zone may output natural light (e.g., daylight toned light) such that the camera 604 above the harvesting zone may capture the image of the plant under natural light. A user may initiate harvesting the plant by pushing the button 740. In response to the push of the Yes button 740, the user computing device 622 may send an instruction to the lifter 450 to push up the upper plate 430 of the industrial cart 104b such that the plant on the industrial cart 104b is dumped out from the industrial cart 104b.

If the user determines that the plant is not ready to harvest, the user may bypass harvesting the plant by pushing the Bypass button 750. In response to pushing the Bypass button 750, the display 700 displays additional buttons for extended growth of the plant. For example, the display 700 displays one day button 752, two days button 754, three days button 756, and four days button 758. If the one day button 752 is selected, the master controller 106 instructs the industrial cart 104b to follow a shortened track which it takes one day for the industrial cart 104b to pass through. Similarly, if the two day button 754 is selected, the master controller 106 instructs the industrial cart 104b to follow a shortened track which is takes two days for the industrial cart 104b to pass through. Examples of shortened tracks will be described below with reference to FIGS. 9 and 10 below.

Referring back to FIG. 6, similar to the user computing device 622, the remote computing device 624 may include a server, personal computer, tablet, mobile device, etc. and may be utilized for machine to machine communications. The remote computing server 624 may store information about carts, identification information about plants on each of carts, weight of plants on each of the carts, height of plants on each of the carts, etc.

Figure 8:
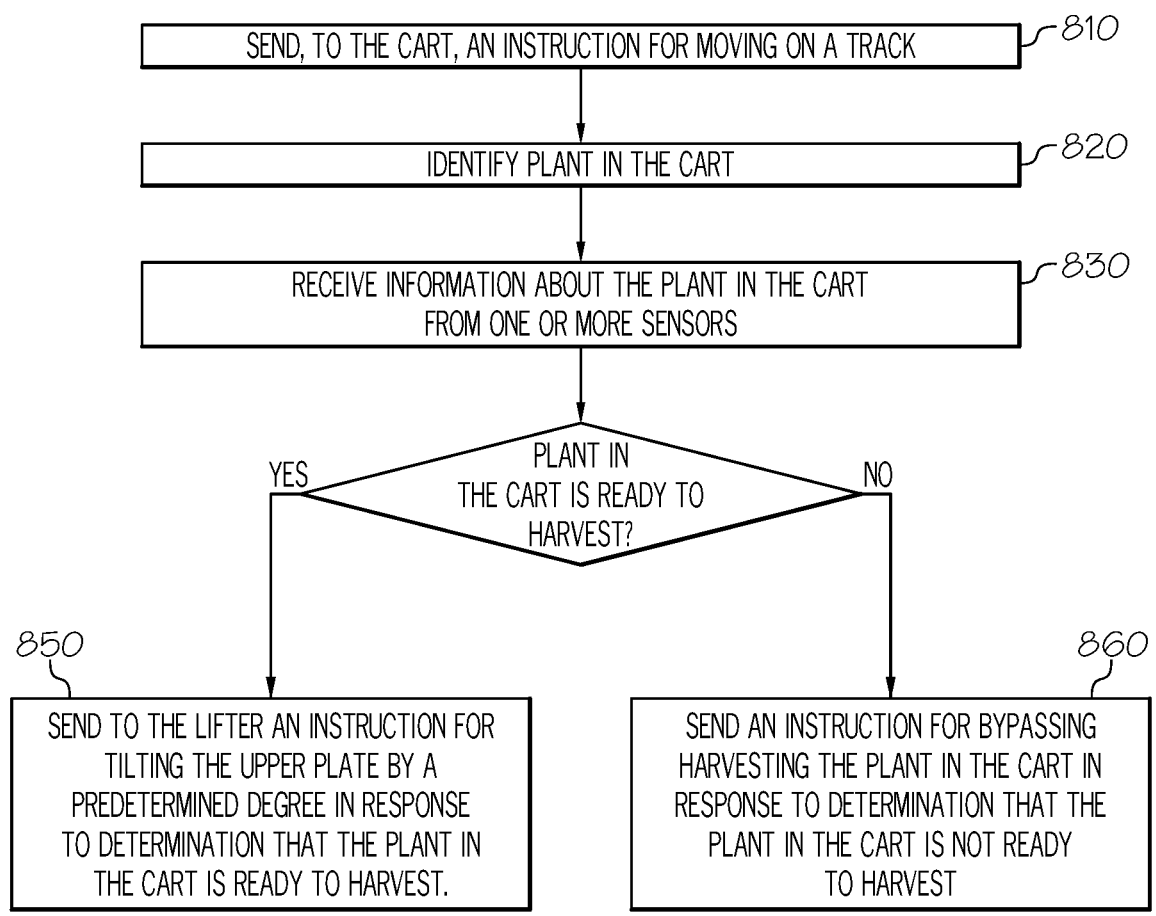
FIG. 8 depicts a flowchart for bypassing harvesting plants in a grow pod, according to embodiments described herein.

FIG. 8 depicts a flowchart for bypassing harvesting plants in a grow pod using sensors, according to one or more embodiments described herein. At block 810, the master controller 106 sends, to industrial carts, an instruction for moving on a track. For example, the master controller 106 instructs the industrial carts 104 to move on the track 102.

At block 820, the master controller 106 identifies plants on a cart. For example, the master controller 106 may communicate with the carts 104a, 104b, and 104c and receive information about the plants in the carts 104a, 104b, and 104c. As another example, the information about the plants in the carts 104a, 104b, and 104c may be pre-stored in the master controller 106 when the seeder component 108 seeds plant A in the carts 104a, 104b, and 104c. Specifically, each of the industrial carts may be assigned to a unique address, and when the seeder component 108 seeds a certain plant into a cart, the unique address of the cart is associated with the information about the certain plant. The association of the unique address and the information about the certain plant may be pre-stored in the master controller 106. For example, the master controller 106 may determine that plant A is in the industrial carts 104a, 104b, and 104c based on the association of the unique addresses for the carts 104a, 104b, and 104c and the information about plant A. As another example, an operator inputs the type of seeds that need to be grown in the carts through the user computing device 622, and the master controller 106 receives the type of seeds from the user computing device 622.

At block 830, the master controller 106 receives data from sensors with respect to corresponding industrial cart. In embodiments, the master controller 106 receives the weight of the plants in the cart 104b from the weight sensor 610b that measures the weight of the plants on the cart 104b in FIG. 6. The master controller 106 may calculate the actual weight of plant by subtracting the weight of water in corresponding cart from the weight received from the weight sensor. In some embodiments, the industrial cart may include sensors for detecting water that has not been absorbed by the plant and detecting an amount of the water. The master controller 106 may estimate the weight of the water in the industrial cart based on data from the sensors for detecting water. For example, the sensors may determine the level of water in the industrial cart 104b, determine the dimension of the water, and calculate the weight of the water based on the dimension. In some embodiments, water in the industrial cart may be removed prior to measuring a weight of the plants as discussed above with reference to FIG. 4. Thus, the weight sensor 610b may accurately measure the weight of the plants in the cart 104b.

In some embodiments, the master controller 106 may also receive data from the proximity sensor 602. For example, the proximity sensor 602 determines the distance between the proximity sensor 602 and the plants in the cart 104b in a z-axis direction, and transmits the distance data to the master controller 106 through the network 620. In some embodiments, the master controller 106 may receive a captured image of the plants on the industrial cart 104b from the camera 604. The camera 604 may capture the image of the plants in the industrial cart 104b. The camera 604 may include a special filter that filters out artificial LED lights from lighting devices in the assembly line grow pod 100 such that the captured image illustrates the natural colors of the plants.

At block 840, the master controller 106 determines whether the plant on the industrial cart 104b is ready to harvest. In embodiments, the master controller 106 determines whether the weight of the plant on the cart is greater than a threshold weight for the identified plant. The threshold value may be a weight of a certain plant in a cart that is grown enough to be harvested. The threshold value may be stored in the plant logic 544b, and the master controller 106 may retrieve the threshold value from the plant logic 544b.

For example, the plant logic 544b of the master controller 106 may store a name of plant and corresponding threshold weight, as shown in Table 1 below.

TABLE 1

| Plant | Threshold weight |
|---|---|
| Plant A | 10 kilograms |
| Plant B | 3 kilograms |
| Plant C | 5 kilograms |
| Plant D | 2 kilograms |

The master controller 106 determines that the plant is ready to harvest if the weight of plant on the cart 104b is greater than the threshold weight. For example, if the weight of the plant A on the industrial cart 104b is 10.8 kilograms, the master controller 106 determines that the plant is ready to harvest because the measured weight is greater than the threshold weight for plant A which is 10 kilograms.

In some embodiments, the master controller 106 determines the average height of the plants based on the data from the proximity sensor 602. If the average height of the plants is greater than a threshold height, the master controller 106 may determine that the plant in the cart 104b is ready to harvest. For example, the plant logic 544b of the master controller 106 may store the name of plant and corresponding threshold average height, as shown in Table 2 below.

TABLE 2

| Plant | Threshold height |
|---|---|
| Plant A | 18 centimeters |
| Plant B | 30 centimeters |
| Plant C | 50 centimeters |
| Plant D | 15 centimeters |

In some embodiments, the master controller 106 estimates the level of chlorophyll of the plant based on the captured image of the plant. For example, the master controller 106 may implement image processing on the captured image of the plant to estimate the level of chlorophyll of the plants. If the level of chlorophyll for the plants in the cart 104b is less than a predetermined value, the master controller 106 may determine that the plant is ready to harvest.

At block 850, the master controller 106 transmits, to the lifter 450, an instruction for tilting the upper plate 430 of the industrial cart 104b such that plant on the upper plate 430 of the industrial cart 104b is dumped out to from the industrial cart 104b in response to determination that the plant is ready to harvest. The lifter 450 pushes up the upper plate 430 of the industrial cart 104b as shown in FIG. 5B in response to receiving the instruction from the master controller 106. In some embodiments, the master controller 106 transmits, to the actuator 530 (FIGS. 5A and 5B), an instruction for tilting the upper plate 430 of the industrial cart 104b such that plant on the upper plate 430 of the industrial cart 104b is dumped out to from the industrial cart 104b. In this regard, the assembly line grow pod 100 allow the plant on carts to be harvested at a proper time (e.g., after the plants are fully grown or ripen).

At block 860, the master controller 106 transmits an instruction for bypassing harvesting the plant in the industrial cart 104b in response to determination that the plant in the industrial cart 104b is not ready to harvest. In embodiments, the master controller 106 may instruct the lifter 450 not to rotate such that the industrial cart 104b continues to carry the plant. In embodiments, the industrial cart 104b which has been bypassed for harvesting may follow a shortened track, which will be described with reference to FIGS. 9 and 10 below. The master controller 106 may determine required growth time to be harvested based on the information about the plant. For example, the master controller 106 may determine that the plant in the industrial cart 104b needs additional two days of growth until being harvested based on the weight, height, and/or chlorophyll level of the plant. Specifically, if the average height of the plant A is 14 centimeters, and it takes average two days for the plant A to be 18 centimeters, the master controller 106 determines that the plant in the industrial cart 104b needs additional two days of growth until being harvested.

Figure 9:
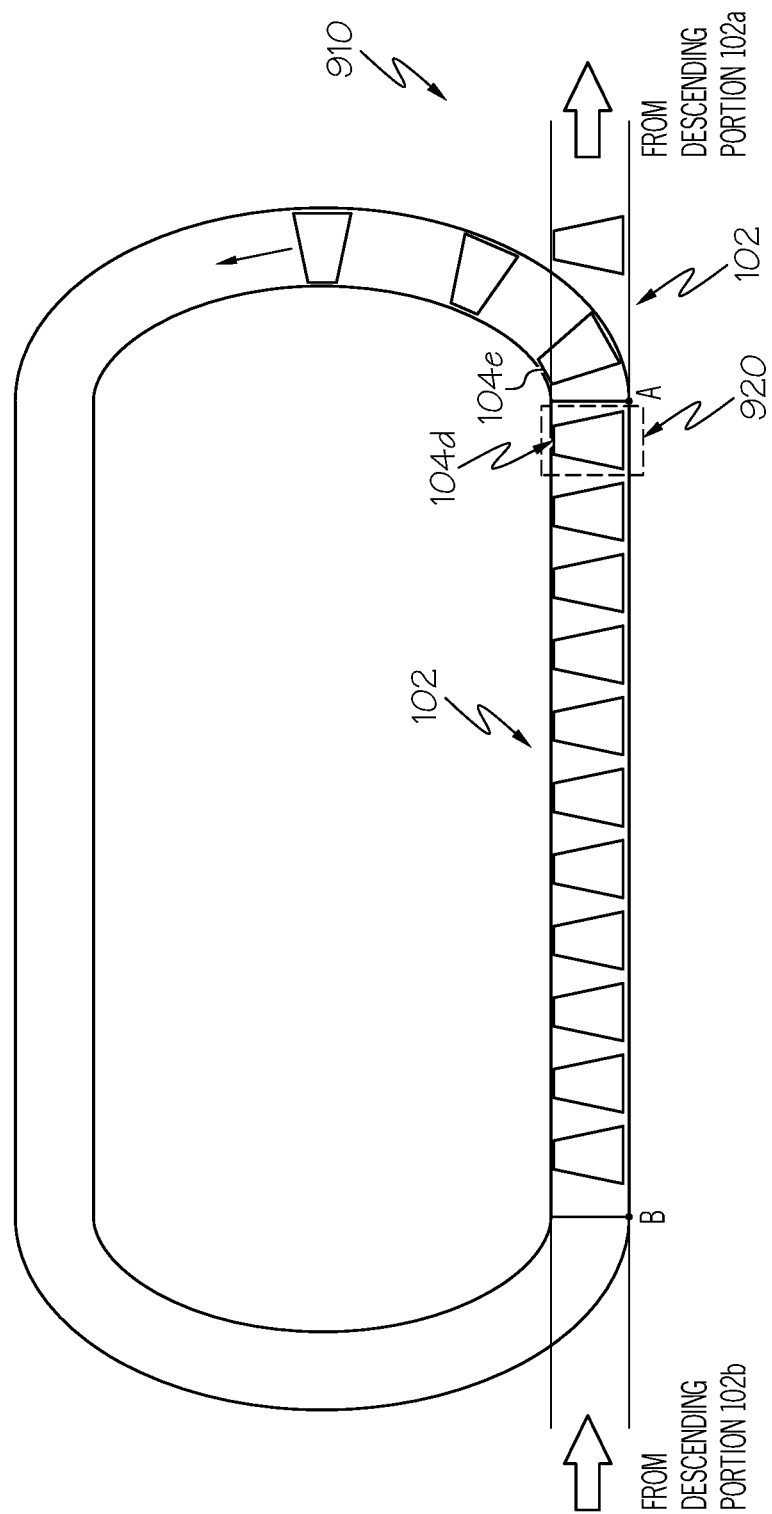
FIG. 9 depicts a top partial view of the assembly line grow pod including an example secondary track, according to embodiments described herein.

FIG. 9 depicts a top partial view of the assembly line grow pod 100 including an example secondary track 910, according to embodiments described herein. The assembly line grow pod 100 includes a secondary track 910 in addition to the track 102 which is a primary track. The secondary track 910 may start at point A and end at point B as illustrated in FIG. 9. At point A, the primary track 102 is bifurcated into the primary track 102 and the secondary track 910. At point B, the secondary track 910 is merged into the primary track 102. The total length of the secondary track may be shorter than the total length of the primary track 102. For example, the total length of the secondary track may be 1/12 of the total length of the primary track, 1/6 of the total length of the primary track, 1/3 of the total length of the primary track, etc. In FIG. 9, the industrial cart 104d is in a harvesting zone 920. If it is determined that the plant in the industrial cart 104d is ready to harvest, the lifter 450 (FIG. 4) rotates to push up the upper plate of the industrial cart 104d such that the plant in the industrial cart 104d is dumped out from the industrial cart 104d. Then, the industrial cart 104d continues to follow the primary track 102, similar to the industrial cart 104f. If it is determined that the plant in the industrial cart 104d is not ready to harvest, the industrial cart 104d continues to carry the plant and follows the secondary track 910 to provide additional simulated growth time for the plant, similar to the industrial cart 104e.

In embodiments, the master controller 106 may instruct a track system of the assembly line grow pod 100 to place carts that bypass harvesting at the harvesting zone 920 onto the secondary track 910 based on the remaining growth time for plants in the carts. For example, if the cart 104d bypasses the harvesting process at the harvesting zone 920, and the remaining growth time for the plants in the cart 104d is less than 6 days, the track for the cart 104d switches from the primary track 102 to the secondary track 910. The cart 104d may move along the secondary track 910 and return to the harvesting zone 920 in less than 6 days, for example, 1 day. In some embodiments, the industrial cart 104d may include a gear system which selects between the primary track 102 and the secondary track 910 to engage with. For example, the master controller 106 may send an instruction for bypassing harvesting to the industrial cart 104d, and the gear system of the industrial cart 104d may engage with and follow the secondary track 910 in response to receiving the instruction.

Lighting devices, watering components, and any other devices for growing plants may be installed proximate to the secondary track 910 for growing plants on the secondary track 910, similar to lighting devices, watering components, and any other devices for the primary track 102. The master controller 106 may control the lighting devices, watering components, and any other devices for growing plants based on the recipe for the plants and/or the growth status of the plants.

In some embodiments, the master controller 106 may control the speed of the industrial cart on the secondary track 910 based on the remaining growth time for the plants in the carts. For example, if the required day of growth for the plant in the industrial cart 104d is one day, and it takes two days for the industrial cart 104d to go through the secondary track 910 and arrive the harvesting zone 920 at a current speed, then the master controller 106 may double the speed of the industrial cart 104d. As another example, if the required day of growth for the plant in the industrial cart 104d is four days, and it takes two days for the industrial cart 104d to go through the secondary track 910 and arrives the harvesting zone 920 at a current speed, then the master controller 106 may reduce the speed of the industrial cart 104d by half. Operations of the lighting devices, watering components, and any other devices may be adjusted based on the adjusted speed of the carts.

Figure 10:
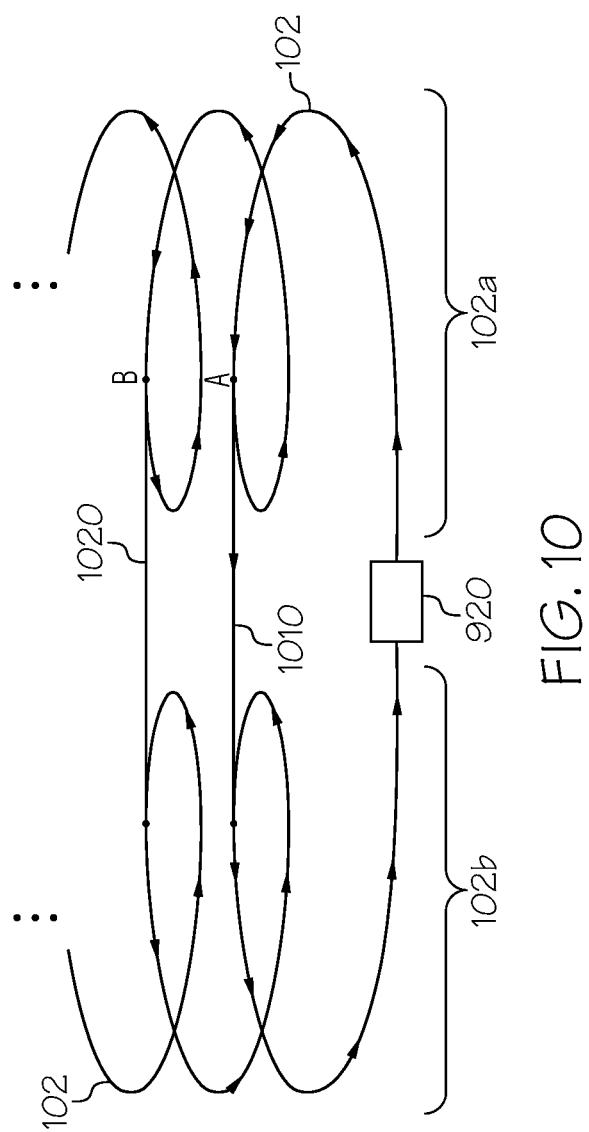
FIG. 10 schematically depicts a part of a primary track and a secondary track of an assembly line grow pod according to embodiments described herein.

FIG. 10 schematically depicts a part of a primary track and a secondary track of an assembly line grow pod 100 according to embodiments described herein. As shown in FIG. 10, the primary track 102 includes the ascending portion 102a and the descending portion 102b. Industrial carts move along the track 102 in a direction indicated by arrows. In embodiments, a secondary track 1010 may be connected between the ascending portion 102a and the descending portion 102b as depicted in FIG. 10. The secondary track 1010 provides a shortened track for industrial carts. For example, it takes one day for an industrial cart to do a lap of the shortened track while it takes six days for the industrial cart to pass through the entire track 102. Specifically, instead of climbing up the entire of the ascending portion 102a shown in FIG. 1, an industrial cart may switch to follow the secondary track 1010 at point A. The industrial cart may follow the primary track 102 after passing through the secondary track 1010.

Another secondary track 1020 may be connected between the ascending portion 102a and the descending portion 102b as depicted in FIG. 10. The secondary track 1020 provides a shortened track for industrial carts. The shortened track provided by the secondary track 1020 is longer than the shorted track provided by the secondary track 1010. For example, it takes two days for an industrial cart to do a lap of the shortened track provided by the secondary track 1020 while it takes one day for the industrial cart to do a lap of the shortened track provided by the secondary track 1010. An industrial cart may switch to follow the secondary track 1020 at point B instead of climbing up the entire of the ascending portion 102a. The industrial cart may follow the primary track 102 after passing through the secondary track 1020. While FIG. 10 depicts two secondary tracks 1010, 1020, more than two secondary tracks may be provided. For example, a secondary track may be provided for each of the stories of the primary track 102.

In embodiments, the master controller 106 may instruct a track system of the assembly line grow pod 100 to place carts that bypass harvesting at the harvesting zone 920 on the secondary track 1010 or the secondary track 1020 based on the remaining growth time for plants in the carts. For example, if an industrial cart bypasses the harvesting process at the harvesting zone 920, and the remaining days of growth for the plants in the cart 104d is one day, the track for the cart 104d switches from the primary track 102 to the secondary track 1010. The cart 104d may move along the secondary track 1010 and return to the harvesting zone 920 in one day. As another example, if an industrial cart bypasses the harvesting process at the harvesting zone 920, and the remaining growth time for the plants in the cart 104d is two days, the track for the cart 104d switches from the primary track 102 to the secondary track 1020. The cart 104d may move along the secondary track 1020 and return to the harvesting zone 920 in two days.

In some embodiments, one of the secondary tracks may be selected based on input from a user. For example, in response to the push of the 2 days button 754 shown in FIG. 7, the master controller 106 may instruct a track system of the assembly line grow pod 100 to place the industrial cart on the secondary track 1020. In response, the industrial cart switches to the secondary track 1020 at point B, and returns to the harvesting zone 920 in two days. As another example, in response to the push of the 1 day button 752 shown in FIG. 7, the master controller 106 may instruct a track system of the assembly line grow pod 100 to place the industrial cart on the secondary track 1010. In response, the industrial cart switches to the secondary track 1010 at point A, and returns to the harvesting zone 920 in one day.

In some embodiments, an industrial cart may include a gear system which selects between the primary track 102 and the secondary track 1010 or the secondary track 1020 to engage with. For example, the master controller 106 may send an instruction for bypassing harvesting to an industrial cart, and the gear system of the industrial cart may engage with and follow the secondary track 1010 or the secondary track 1020 at point A or point B in response to receiving the instruction.

FIG. 11 depicts a computing device 130 for an assembly line grow pod 100, according to embodiments described herein. As illustrated, the computing device 130 includes a processor 930, input/output hardware 932, the network interface hardware 934, a data storage component 936 (which stores systems data 938a, plant data 938b, and/or other data), and the memory component 540. The memory component 540 may be configured as volatile and/or non-volatile memory and as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the computing device 130 and/or external to the computing device 130.

The memory component 540 may store operating logic 942, the systems logic 544a, and the plant logic 544b. The systems logic 544a and the plant logic 544b may each include a plurality of different pieces of logic, each of which may be embodied as a computer program, firmware, and/or hardware, as an example. A local interface 946 is also included in FIG. 9 and may be implemented as a bus or other communication interface to facilitate communication among the components of the computing device 130.

The processor 930 may include any processing component operable to receive and execute instructions (such as from a data storage component 936 and/or the memory component 540). The input/output hardware 932 may include and/or be configured to interface with microphones, speakers, a display, and/or other hardware.

The network interface hardware 934 may include and/or be configured for communicating with any wired or wireless networking hardware, including an antenna, a modem, LAN port, wireless fidelity (Wi-Fi) card, WiMax card, ZigBee card, Bluetooth chip, USB card, mobile communications hardware, and/or other hardware for communicating with other networks and/or devices. From this connection, communication may be facilitated between the computing device 130 and other computing devices, such as the user computing device 622 and/or remote computing device 624.

The operating logic 942 may include an operating system and/or other software for managing components of the computing device 130. As also discussed above, systems logic 544a and the plant logic 544b may reside in the memory component 540 and may be configured to perform the functionality, as described herein.

It should be understood that while the components in FIG. 11 are illustrated as residing within the computing device 130, this is merely an example. In some embodiments, one or more of the components may reside external to the computing device 130. It should also be understood that, while the computing device 130 is illustrated as a single device, this is also merely an example. In some embodiments, the systems logic 544a and the plant logic 544b may reside on different computing devices. As an example, one or more of the functionalities and/or components described herein may be provided by the user computing device 622 and/or remote computing device 624.

Additionally, while the computing device 130 is illustrated with the systems logic 544a and the plant logic 544b as separate logical components, this is also an example. In some embodiments, a single piece of logic (and/or or several linked modules) may cause the computing device 130 to provide the described functionality.

As illustrated above, various embodiments for harvesting plants in a grow pod are disclosed. These embodiments create a quick growing, small footprint, chemical free, low labor solution to growing microgreens and other plants for harvesting. These embodiments may create recipes and/or receive recipes that dictate the timing and wavelength of light, pressure, temperature, watering, nutrients, molecular atmosphere, and/or other variables the optimize plant growth and output. The recipe may be implemented strictly and/or modified based on results of a particular plant, tray, or crop.

Accordingly, some embodiments may include a system for bypassing harvesting. The system includes a track, a cart configured to move on the track, the cart including an upper plate configured to support a plant, one or more sensors and a controller. The controller includes one or more processors, one or more memory modules, and machine readable instructions stored in the one or more memory modules that, when executed by the one or more processors, cause the controller to: receive information about the plant from the one or more sensors, determine whether the plant in the cart is ready to harvest based on the information; and transmit an instruction for bypassing harvesting the plant in the cart in response to determination that the plant in the cart is not ready to harvest. The track may include a primary track, and a secondary track connected to the primary track. The controller may transmit an instruction for switching a path of the cart from the primary track to the secondary track in response to determination that the plant in the cart is not ready to harvest. The system according to the present disclosure bypasses harvesting plants and selectively provided extended period of growth for the plants. As such, every plant may be fully grown before being harvested in an assembly line grow pod.

While particular embodiments and aspects of the present disclosure have been illustrated and described herein, various other changes and modifications can be made without departing from the spirit and scope of the disclosure. Moreover, although various aspects have been described herein, such aspects need not be utilized in combination. Accordingly, it is therefore intended that the appended claims cover all such changes and modifications that are within the scope of the embodiments shown and described herein.

It should now be understood that embodiments disclosed herein includes systems, methods, and non-transitory computer-readable mediums for harvesting plants. It should also be understood that these embodiments are merely exemplary and are not intended to limit the scope of this disclosure.

What is claimed is:

1. A system for bypassing harvesting in an assembly line grow pod, the system comprising:
at least one track including a harvesting zone and a growing zone, the at least one track being a closed loop track;
a cart configured to move on the track, the cart including an upper plate configured to support a plant;
one or more sensors; and a controller comprising:
one or more processors;
one or more memory modules; and
machine readable instructions stored in the one or more memory modules that, when executed by the one or more processors, cause the controller to:
receive information about the plant from the one or more sensors;
determine whether the plant in the cart is ready to harvest based on the information; and
transmit an instruction for bypassing harvesting the plant in the cart at the harvesting zone and instruct the cart to move to the growing zone of the at least one track after passing the harvesting zone in response to determination that the plant in the cart is not ready to harvest.

2. The system of claim 1, wherein the at least one track comprises:
a primary track; and
a secondary track connected to the primary track, and wherein the instruction for bypassing harvesting includes an instruction for switching a path of the cart from the primary track to the secondary track.

3. The system of claim 2, wherein a total length of the secondary track is shorter than a total length of the primary track.

4. The system of claim 2, wherein the machine readable instructions stored in the one or more memory modules, when executed by the one or more processors, cause the controller to:
determine additional growth time for the plant based on the information about the plant in response to determination that the plant in the cart is not ready to harvest; and
control a speed of the cart on the secondary track based on the additional growth time.

5. The system of claim 2, wherein the primary track includes an ascending portion wrapping around a first axis perpendicular to ground and a descending portion wrapping around a second axis perpendicular to the ground.

6. The system of claim 5, wherein:
the ascending portion is bifurcated into a spiral track and a linear track,
the linear track is connected to the descending portion, and
the secondary track includes the linear track.

7. The system of claim 1, wherein the at least track comprises:
a primary track; and
a plurality of secondary tracks connected to the primary track, and
the machine readable instructions stored in the one or more memory modules, when executed by the one or more processors, cause the controller to:
determine additional growth time for the plant based on the information about the plant in response to determination that the plant in the cart is not ready to harvest; and
select one of the plurality of secondary tracks based on the additional growth time.

8. The system of claim 1, further comprising a lifter, wherein the machine readable instructions stored in the one or more memory modules, when executed by the one or more processors, cause the controller to send to the lifter an instruction for tilting the upper plate by a predetermined degree in response to determination that the plant in the cart is ready to harvest.

9. The system of claim 1, wherein the one or more sensors include a proximity sensor, and the machine readable instructions stored in the one or more memory modules, when executed by the one or more processors, cause the controller to calculate a height of the plant in the cart based on information received from the proximity sensor.

10. The system of claim 1, wherein the one or more sensors include a weight sensor, and the machine readable instructions stored in the one or more memory modules, when executed by the one or more processors, cause the controller to determine a weight of the plant in the cart based on information received from the weight sensor.

11. The system of claim 1, wherein the one or more sensors include a camera configured to capture an image of the plant, and the machine readable instructions stored in the one or more memory modules, when executed by the one or more processors, cause the controller to:
process the image received from the camera; and
determine a chlorophyll level of the plant based on the processed image.

12. The system of claim 1, wherein the machine readable instructions stored in the one or more memory modules, when executed by the one or more processors, cause the controller to:
determine additional growth time for the plant based on the information about the plant in response to determination that the plant in the cart is not ready to harvest; and
select a secondary track based on the additional growth time.

13. A controller for bypassing harvesting a plant in a cart, the controller comprising:
one or more processors;
one or more memory modules; and
machine readable instructions stored in the one or more memory modules that, when executed by the one or more processors, cause the controller to:
send, to the cart, an instruction for moving on at least one track including a harvesting zone and a growing zone, the at least one track being a closed loop track;
receive information about the plant in the cart from one or more sensors;
determine whether the plant in the cart is ready to harvest based on the information; and
transmit an instruction for bypassing harvesting the plant in the cart at the harvesting zone and instruct the cart to move to the growing zone of the at least one track after passing the harvesting zone in response to determination that the plant in the cart is not ready to harvest.

14. The controller of claim 13, wherein the at least track comprises:
a primary track; and
a secondary track connected to the primary track, and wherein the instruction for bypassing harvesting includes an instruction for switching a path of the cart from the primary track to the secondary track.

15. The controller of claim 14, wherein the machine readable instructions stored in the one or more memory modules, when executed by the one or more processors, cause the controller to:
determine additional growth time for the plant based on the information about the plant in response to determination that the plant in the cart is not ready to harvest; and
control a speed of the cart on the secondary track based on the additional growth time.

16. The controller of claim 13, wherein the at least track comprises:
- a primary track; and
- a plurality of secondary tracks connected to the primary track, and
  - the machine readable instructions stored in the one or more memory modules, when executed by the one or more processors, cause the controller to:
- determine additional growth time for the plant based on the information about the plant in response to determination that the plant in the cart is not ready to harvest; and
- select one of the plurality of secondary tracks as a path for cart based on the additional growth time.

17. A method for bypassing harvesting a plant in a cart comprising:
- sending, to the cart, an instruction for moving on at least one track including a harvesting zone and a growing zone, the at least one track being a closed loop track;
- receiving information about the plant in the cart from one or more sensors;
- determining whether the plant in the cart is ready to harvest based on the information; and
- transmitting an instruction for bypassing harvesting the plant in the cart at the harvesting zone and instructing the cart to move to the growing zone of the at least one track after passing the harvesting zone in response to determination that the plant in the cart is not ready to harvest.

18. The method of claim 17, wherein the instruction for bypassing harvesting includes an instruction for switching a path of the cart from a primary track of the at least one track to a secondary track of the at least one track.

19. The method of claim 17, further comprising:
- determining additional growth time for the plant based on the information about the plant in response to determination that the plant in the cart is not ready to harvest; and
- selecting one of a plurality of secondary tracks as a path for the cart based on the additional growth time.

20. The method of claim 17, further comprising:
- determine additional growth time for the plant based on the information about the plant in response to determination that the plant in the cart is not ready to harvest; and
- controlling a speed of the cart on a secondary track connected to the at least one track based on the additional growth time.

* * * * *